United States Patent
Tedesco et al.

(10) Patent No.: US 10,739,304 B2
(45) Date of Patent: Aug. 11, 2020

(54) ORGANIC TRANSISTOR-BASED SYSTEM FOR ELECTROPHYSIOLOGICAL MONITORING OF CELLS AND METHOD FOR THE MONITORING OF THE CELLS

(71) Applicants: UNIVERSITA DEGLI STUDI DI CAGLIARI, Cagliari (IT); UNIVERSITA DEGLI STUDI DI GENOVA, Genoa (IT)

(72) Inventors: MariaTeresa Tedesco, Genoa (IT); Annalisa Bonfiglio, Leivi (IT); Andrea Spanu, Cagliari (IT); Stefano Lai, Cagliari (IT); Sergio Martinoia, Genoa (IT); Piero Cosseddu, Cagliari (IT)

(73) Assignee: UNIVERSITA DEGLI STUDI DI CAGLIARI, Genoa (IT)

( * ) Notice: Subject to any disclaimer, the term of this patent is extended or adjusted under 35 U.S.C. 154(b) by 273 days.

(21) Appl. No.: 15/548,837

(22) PCT Filed: Feb. 4, 2016

(86) PCT No.: PCT/EP2016/052433
§ 371 (c)(1),
(2) Date: Aug. 4, 2017

(87) PCT Pub. No.: WO2016/124714
PCT Pub. Date: Aug. 11, 2016

(65) Prior Publication Data
US 2018/0031520 A1    Feb. 1, 2018

(30) Foreign Application Priority Data
Feb. 4, 2015    (IT) .............................. MI2015A0145

(51) Int. Cl.
*G01N 27/414* (2006.01)
*G01N 33/483* (2006.01)

(52) U.S. Cl.
CPC ..... *G01N 27/4145* (2013.01); *G01N 33/4833* (2013.01)

(58) Field of Classification Search
CPC .............. G01N 27/414–4148; G01N 33/4833
See application file for complete search history.

(56) References Cited

U.S. PATENT DOCUMENTS

2012/0265474 A1    10/2012    Rearick et al.

OTHER PUBLICATIONS

A. Sapnu, et al. ("Organic FET device as a novel sensor for cell bioelectrical and metabolic activity recordings", In 2013—6th International IEEE/EMBS Conference on Neural Engineering (NER), p. 937-940, Nov. 2013.*

(Continued)

*Primary Examiner* — J. Christopher Ball
(74) *Attorney, Agent, or Firm* — Volpe and Koenig, P.C.

(57) ABSTRACT

An organic transistor-based system for electrophysiological monitoring of cells is disclosed. The system includes a plurality of organic transistors each comprising: a floating gate electrode; a source electrode and a drain electrode; an organic semiconductor; an insulating layer; and a sensing area. A barrier mechanically separates said sensing area and a transistor area. Each organic transistor includes a control gate electrode coupled to a second portion of said floating gate electrode external to said sensing area by a capacitor. The control gate electrode is separated from said floating gate electrode by said insulating layer. The control gate electrode sets a working point of the organic transistor to which the control gate electrode belongs to by a control voltage ($V_{GS}$) applied to it. In each organic transistor, an overlapping area defined by said control gate electrode formed above said floating gate is comprised between $9*10^{-4}$ cm² and $2*10^{-3}$ cm².

26 Claims, 10 Drawing Sheets

(56) References Cited

OTHER PUBLICATIONS

P. Cosseddu, et al. ("A Temperature Transducer Based on a Low-Voltage Organic Thin-Film Transistor Detecting Pyroelectric Effect", IEEE Electron Device Letters, 35(12): p. 1296-1298, Oct. 2014.*

A. Spanu, et al. ("A high-sensitivity tactile sensor based on piezoelectric polymer PVDF coupled to an ultra-low voltage organic transistor", Organic Electronics, 36, p. 57-60, Sep. 2016.*

A. Caboni, et al. "Flexible Organic Thin-Film Transistors for pH Monitoring", IEEE Sensors Journal, 9(12): p. 1963-1970, Dec. 2009.*

A. Spanu et al. "An organic transistor-based system for reference-less electrophysiological monitoring of excitable cells" Scientific Reports, vol. 5, Mar. 6, 2015.

S. Lai et al. "Ultralow Voltage, OTFT-Based Sensor for Label-Free DNA Detection", Advanced Materials, vol. 25, No. 1, Jan. 4, 2013.

A. Lambacher et al., "Electrical imaging of neuronal activity by multi-transistor-array (MTA) recording at 7.8 mum resolution", Applied Physics A: Materials Science & Processing, Springer International, DE, vol. A79, No. 7, Nov. 1, 2004.

G. Zeck et al., "Noninvasive neuroelectronic interfacing with synaptically connected snail neurons immobilized on a semiconductor chip", Proceedings of the National Academy of Sciences, National Academy of Sciences, U.S., vol. 98, No. 18, Aug. 28, 2001.

Monia Demelas et al. "Charge sensing by organic charge-modulated field effect transistors: application to the letection of bio-related effects", Journal of Materials Chemistry B, vol. 1, No. 31, Jan. 1, 2013.

Stefano Lai et al., "Ultralow Voltage Pressure Sensors Based on Organic FETs and Compressible Capacitors" IEEE Electron Device Letters, IEEE Service Center, New York, NY, US vol. 34, No. 6, Jun. 1, 2013.

Fabrizio Antonio Viola et al. "Flexible temperature sensors based on charge modulated organic thin film transistors" 2015 11th Conference on PHD.D. Research in Microelectronics and Electronics (Prime), Jun. 1, 2015.

"A transparent organic transistor structure for bidirectional stimulation and recording of primary neurons." Benfenati et al. Nature Material, 12, 672-680 (2013).

"Functional and Structural Assessment of Intercellular Communication; Increased Conduction Velocity and Enhanced Connexin Expression in Dibutyryl cAMP—Treated Cultured Cardiac Myocytes." Darrow et al. Circ. Res. 79, 174-183 (1996).

"In vivo recordings of brain activity using organic transistors." Khodagholy et al. Nature Communication, 4 (2013).

"Towards high frequency performances of ultra-low voltage OTFTs: Combining self-alignment and hybrid, nanosized dielectrics." Lai, S. et al. Organic Electronics 14, 754-761 (2013).

"Stimulation of hypertrophy of cultured neonatal rat heart cells through an alpha 1-adrenergic receptor and induction of beating through an alpha 1- and beta 1-adrenergic receptor interaction. Evidence for independent regulation of growth and beating." Paul Simpson; Circ. Res. 56, 884-894 (1985).

"Organic electronics for precise delivery of neurotransmitters to modulate mammalian sensory function." Simon D.T. et al, Nature Material 8, 742-746 (2009).

"Effects of calcium antagonist on β-receptors of cultured cardiac myocytes isolated from neonatal rat ventricle." Yonemochi, H. et al. Circulation 81, 1401-1408 (1990).

* cited by examiner

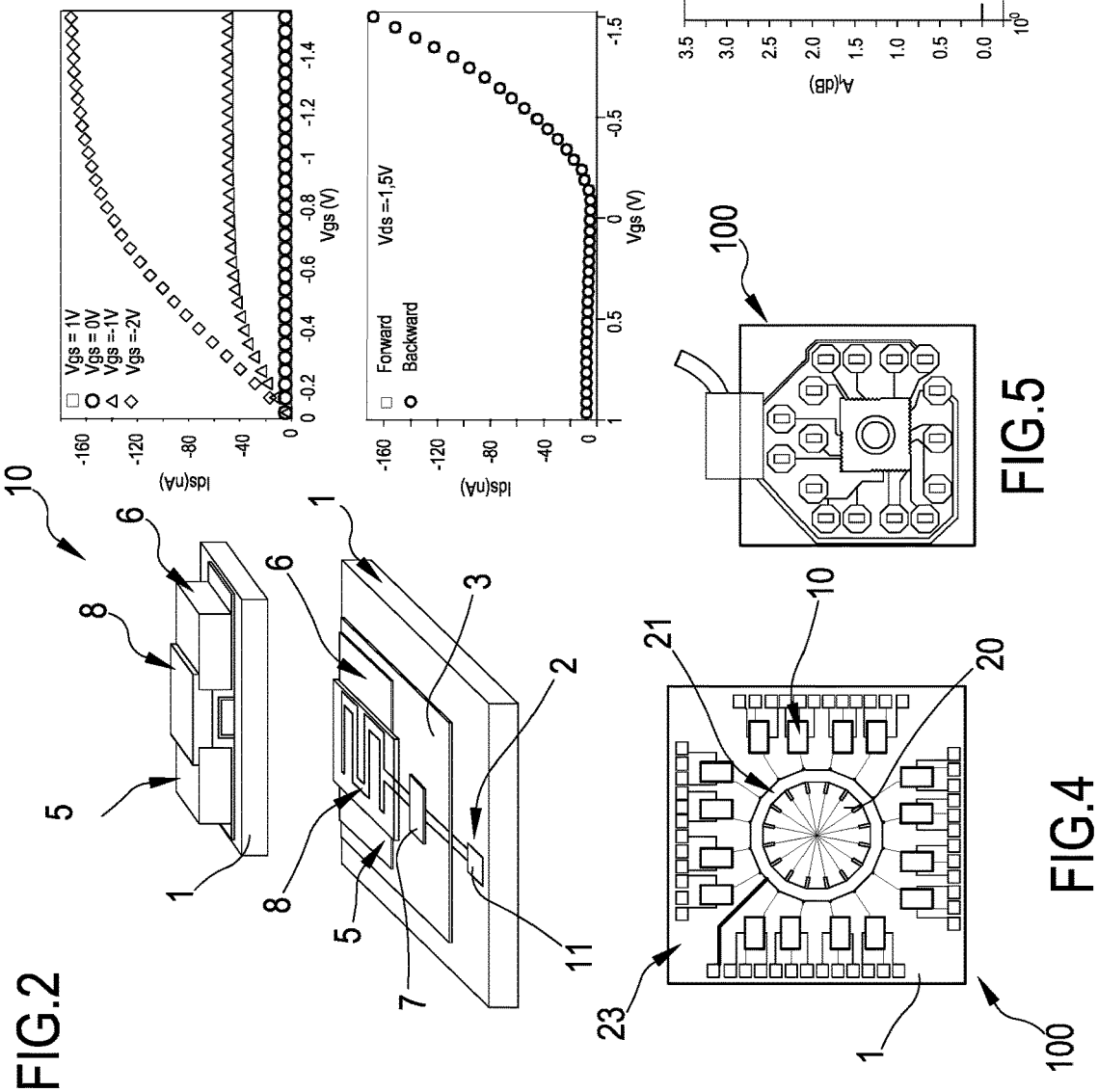

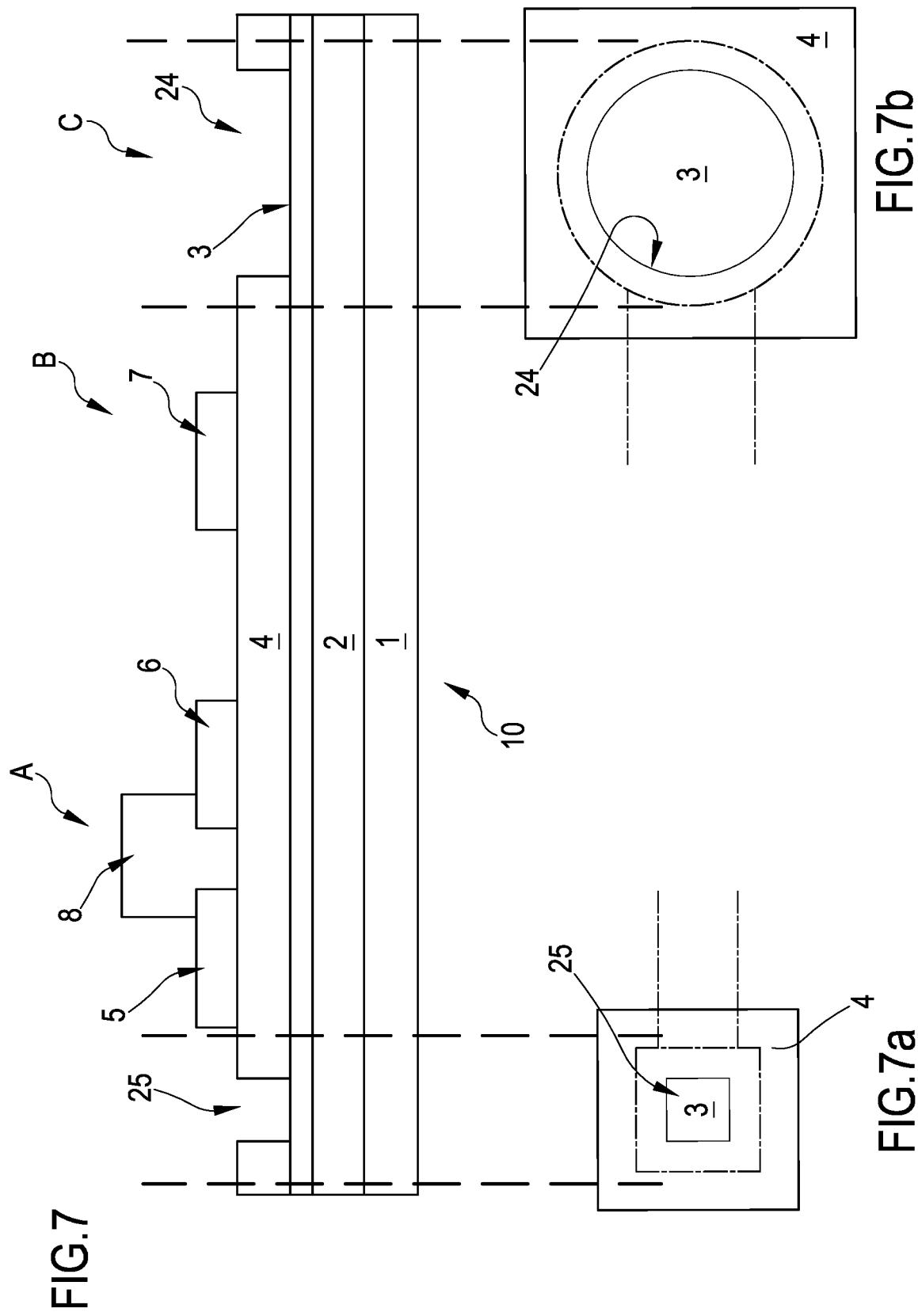

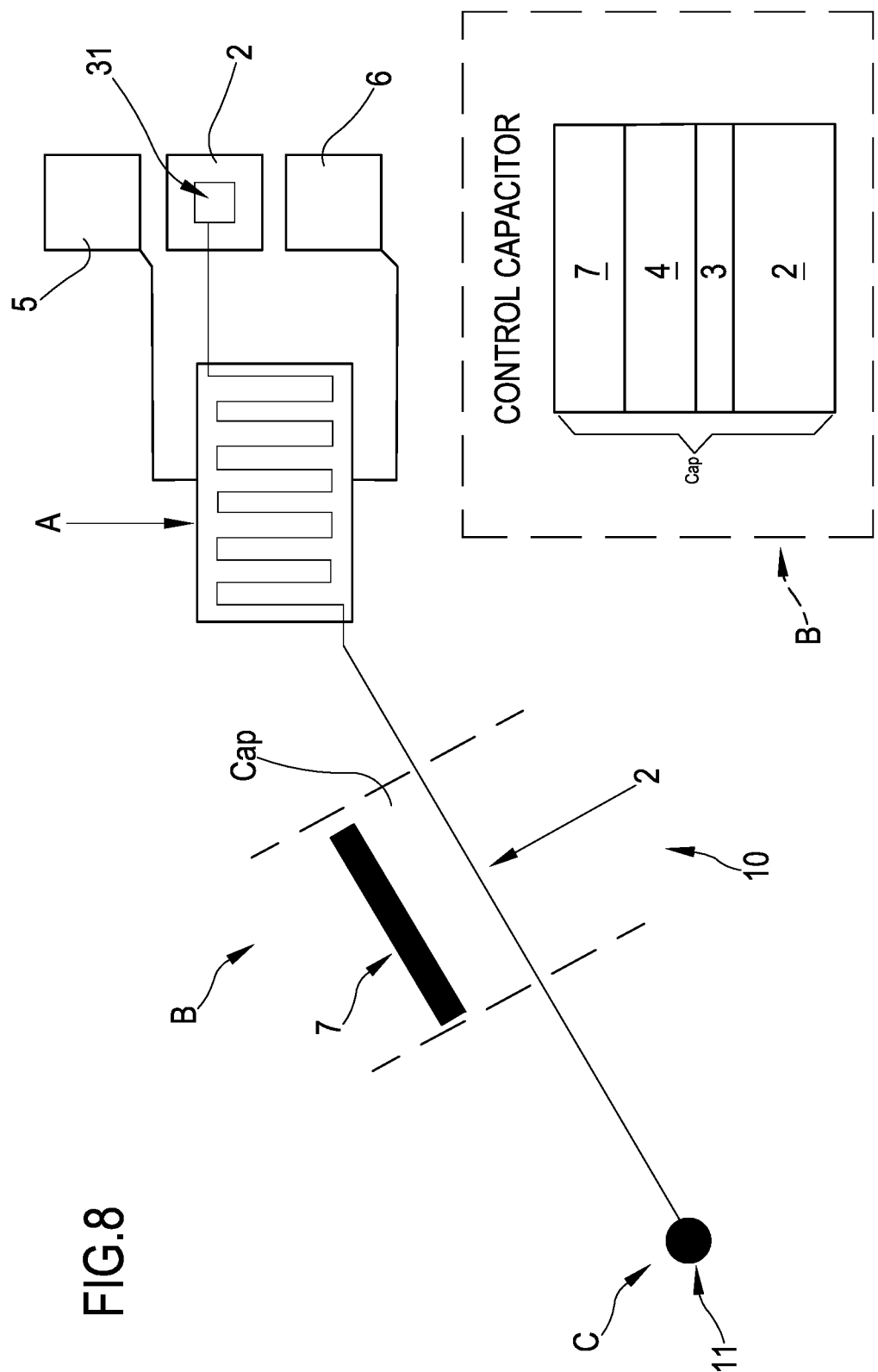

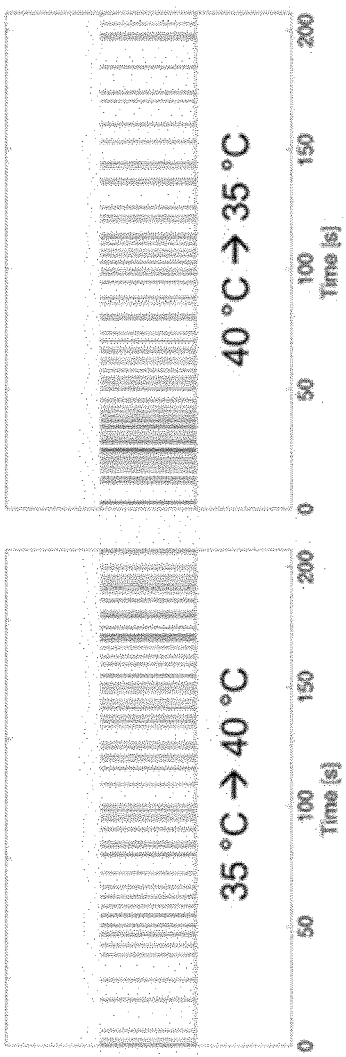
FIG. 14
FIG. 15
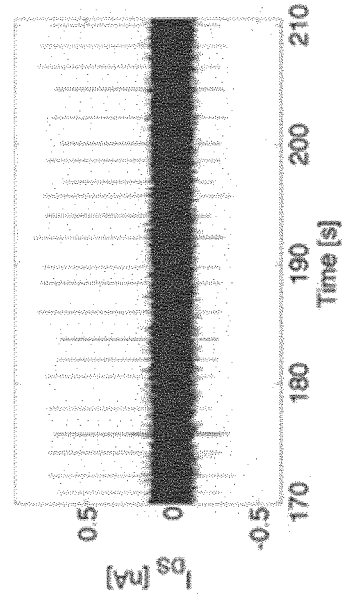
FIG. 16
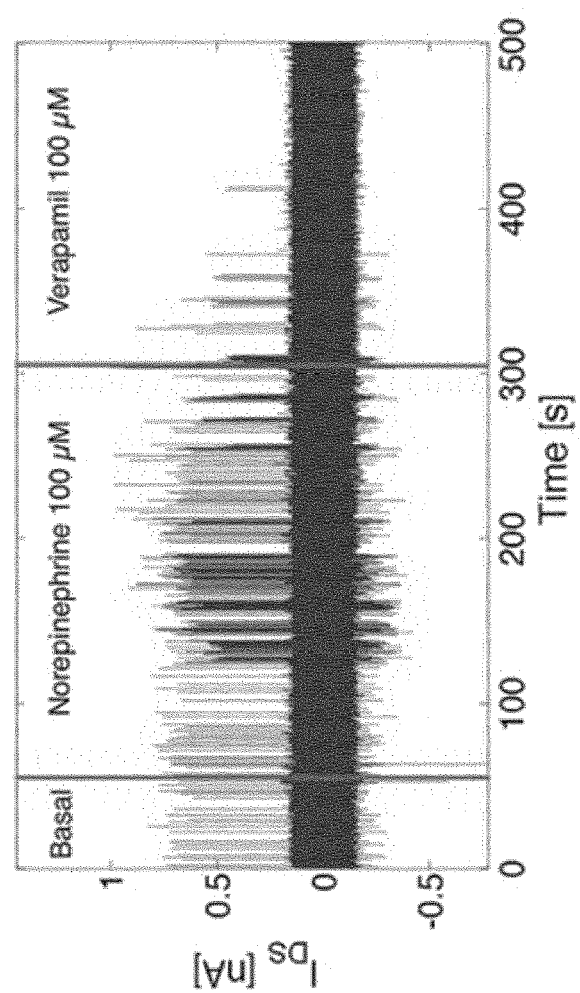
FIG. 17
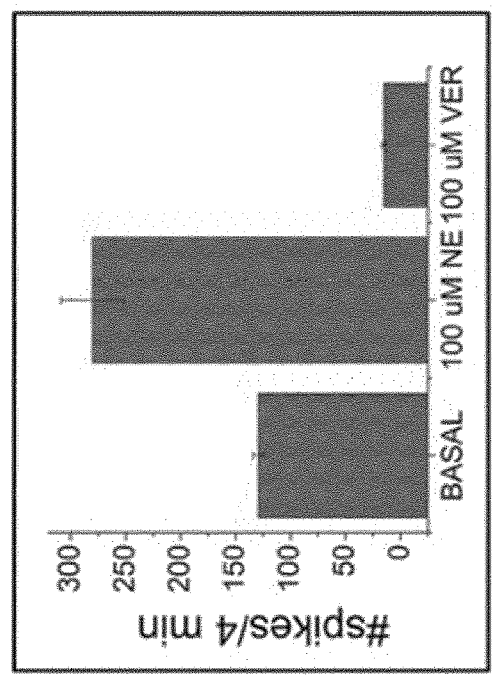

ORGANIC TRANSISTOR-BASED SYSTEM FOR ELECTROPHYSIOLOGICAL MONITORING OF CELLS AND METHOD FOR THE MONITORING OF THE CELLS

CROSS REFERENCE TO RELATED APPLICATION

This application is a 371 National Phase filing of PCT/EP2016/052433 with an International Filing Date of Feb. 4, 2016, which claims priority to Italian Patent Application No. MI2015A000145, filed Feb. 4, 2015, which are incorporated herein by reference as if fully set forth.

FIELD OF INVENTION

The present invention is relative to an organic transistor-based system conceived for monitoring living cells and to a method to perform such monitoring. The system and the method provide a tool to detect dynamic, relatively small, charge variations, such as those related to electrophysiological activity, with high accuracy.

BACKGROUND

The effective connection between cellular tissues and technological platforms is crucial for the success of many bionic applications as neural prostheses and hybrids for studying information processing in neuronal networks. Moreover, the recent attention for disposable, low-cost and reliable cell-to-chip interface systems for high-throughput in-vitro toxicity assays and pharmacology is becoming an urgent request because of the new international regulatory test guidelines (both in Europe and USA). Therefore, engineering the so-called bio-electronic interface is the subject of many technological and basic/applied researches. Specifically related to the cell (neuronal)-electronic interface, two different kinds of devices have been extensively used over the past thirty years, namely microelectrodes arrays and field-effect devices.

More recently, organic semiconductors have attracted a considerable interest in this field (see for example Simon D. T. et al, *Nature Material* 8, 742-746 (2009)) because they have the potential to fulfill many critical requirements for biomedical and biotechnological applications such as biological compatibility, mechanical flexibility, and optical transparency. Moreover, devices based on organic semiconductors can be fabricated on flexible low-cost plastic substrates, with micrometric resolution, over large areas, and using cost-efficient technologies. All these features could allow addressing a wide variety of novel applications ranging from in-vitro to in-vivo cell biology and addressing unsolved problems of mechanical adaptability (e.g., high density flexible transducers on catheters) or of multi-parameters analysis on a micro-scale (e.g., disposable and sensorized smart-Petri dish). So far, in addition to passive electrodes made of organic conductive polymers, organic electrochemical transistors (OECTs) have been mainly proposed (See e.g. Khodagholy et al. *Nature Communication,* 4 (2013)) because of their ability to conduct ionic and electronic charges and to be operated in liquid at very low voltages, which represents a crucial requirement in presence of living cells or tissues. Organic Thin Film Transistors (OTFTs) have not yet been employed so far to this aim for two main reasons: 1) they usually need to be operated at relatively high voltages (usually tens of volts); 2) charge carrier mobility in organic semiconductors is generally orders of magnitude smaller than what generally measured in their standard inorganic counterparts, putting a limit on the frequency range of the electrical signals that might be applied as input for organic amplifiers.

A very recent attempt has been done (Benfenati et al. *Nature Material,* 12, 672-680 (2013)) but, as a matter of fact, the organic transistor employed in the reported experiments is always operated in the off-state and therefore, this cannot be described as an actual amplifying transducer for the cell activity.

SUMMARY

The goal of the present invention is to render available an optimized system, preferably based on a plurality of organic thin film transistors, which is able to measure, extracellularly, the electrophysiological signal(s) of living cells. Further, a method for such monitoring is also encompassed by the present invention. The invention relates also to a method to electrically excite such cells by means of a stimulus and optionally measure the response to the stimulus.

In order to measure signals coming from living cells, the system of the invention is preferably operated at low voltages, that is voltages preferably in a range of about 0.5 V and about 2 V. Further, the method and the system work without any external reference electrode. Not least, preferably the method and system amplify signals in the frequency range of cell electrical activity, that is, preferably in a range between 1 Hz and 1000 Hz (operating range of the signals coming from cells).

According to a first aspect, the invention relates to an organic transistor-based system for electrophysiological monitoring of cells including:

A transistor area including a plurality of organic transistors, each organic transistor of the plurality comprising:
  A floating gate electrode;
  a source electrode and a drain electrode;
  an organic semiconductor;
  an insulating layer fabricated between said source and drain electrodes, and said floating gate electrode, said insulating layer having either a thickness comprised between about 1 nm and about 100 nm or a capacitance per unit area comprised between about 10 nF/cm$^2$ and about 150 nF/cm$^2$;

A sensing area, said sensing area including a biocompatible layer realized in an insulating biocompatible material, said layer being apt to be in contact with said cells to be monitored and covering a first portion of floating gate electrodes of the plurality of organic transistors, said biocompatible layer including a plurality of through apertures, each aperture exposing a portion of the floating gate electrode of an organic transistor of the plurality, so that the floating gates of at least some of the organic transistors are exposed in said sensing area in order to be in contact with said cells to be monitored;

A barrier mechanically separating said sensing area and the transistor area;

each of said organic transistors of said plurality further including a control gate electrode coupled to a second portion of said floating gate electrode external to said sensing area by means of a capacitor, said control gate electrode being separated from said floating gate electrode by said insulating layer, said control gate electrode being apt to set a working point of the organic transistor to which the control gate electrode belongs to by a control voltage applied to it;

wherein, in each organic transistor, an overlapping area defined by said control gate electrode formed above said floating gate is comprised between $9*10^{-4}$ cm$^2$ and $2*10^{-3}$ cm$^2$.

According to a second aspect, the invention related to a method to detect cells' electrical activity, said cells being positioned onto a sensing area, by means of a system realized according to the first aspect of the invention, the method comprising the steps of:
setting a working point of each organic transistor applying a voltage to the respective control gate electrode belonging to each organic transistor;
measuring the drain current of each organic transistor of the plurality;
checking the variations of the drain current of each organic transistor caused by charge re-distribution in the corresponding floating gate electrode due to cells' electrical activity.

The system of the invention includes a sensing area. The sensing area is the location where the cells are positioned and/or cultured. The monitoring of the cells can be performed for example also in-vivo or on slices of tissue, such as on slices of brain. The signals coming from these cells are considered as variations of electrical charge, and are sensed using a plurality of transistors. The sensing area is insulated from the active channel of each of the transistors by means of a barrier, so as to avoid several drawbacks related to the measurement of signals in liquid environments by means of organic devices, such as, for instance, the poor stability of organic semiconductors when exposed to moisture and oxygen.

The system therefore includes a sensing area which is physically separated by the area where the transistors are present, called transistor area, by a mechanical barrier.

The mechanical barrier of the sensing area is preferably formed or covered by a biocompatible material such as Teflon, PLA, ABS, PET, PDMS and combination thereof. Further, preferably the area of the sensing area is comprised between 1 cm2 and 5 cm2. Alternatively or in addition, the volume which is confinable within the sensing area (and therefore the value given by the area of the sensing area multiplied by the height of the barrier) is preferably comprised between 0.5 ml and 2 ml. Preferably, the sensing area is substantially circular, however other configurations are possible as well.

Each transistor is preferably an organic thin-film transistor and—as usual—includes three-terminal devices comprising gate (G), source (S) and drain (D) electrodes. The gate electrode of each transistor of the plurality is electrically isolated, creating a floating gate. This isolation is achieved by interposing an insulating layer between the floating gate electrode and the drain/source electrodes. Further, each transistor includes a control gate electrode (CG). The control gate and floating gate electrodes are electrically isolated one from the other, for example by means of the insulating layer (the same as the one interposed between the floating gate electrode and the drain/source electrodes or a different one). Further, in the plurality of organic transistors, the control gate electrodes are all electrically isolated one from the others. The control gate electrode is capacitively connected to the floating gate electrode.

As mentioned, each transistor of the plurality is an organic transistor, in which an organic semiconductor is deposited to bridge the source and drain electrodes. Preferably the organic transistor is itself spaced from the floating gate electrode by an insulating layer, the same or another already described above. The organic semiconductor can be a pi-conjugated polymer or oligomer. A voltage VGS is applied to the control gate electrode to control the amount of charge accumulation at the interface between the semiconductor and the insulating layer; a voltage VDS is applied between the drain and the source to induce the current flow (IDS) between the source and drain.

In the following:

$V_{GS}$: voltage applied between the control gate and the source electrodes;

$V_{DS}$: voltage applied between the source and the drain electrodes;

$V_{FG}$: voltage at the floating gate electrode.

Preferably $0<V_{DS}\leq 3$ Volt, and/or preferably $0<V_{GS}\leq 3$ Volt.

The transistor indeed controls the flow of electrons (or electron holes) from the source to the drain by affecting the charge density of a "conductive channel", in this case the organic semiconductor, created and influenced by voltage (or lack of voltage) applied across the control gate and source electrodes.

The control gate electrode therefore sets the working point of the transistor by means of a control voltage applied to it.

The control voltage applied to it means in an embodiment of the system and/or the method of the invention the voltage VGS applied between the control gate electrode and the source electrode. For example the source electrode can have a potential equal to zero, so this voltage difference VGS=VCG applied at the control gate electrode.

The "working point" in this specific case refers to the source-drain current, also called output current of the transistor. The voltage applied to the control gate sets the static drain output current of the transistor ("static" in the sense that this current is measured not during the phase of measuring the cells' activity). Therefore, by applying a voltage to the control gate electrode, a pre-determined output current of each transistor can be set.

The organic semiconductor forming the channel can be any semiconductor used in the field for the realization of organic transistor. As examples, the organic semiconductor may include an aromatic or otherwise conjugated n-electron system, facilitating the delocalization of orbital wave-functions. Electron withdrawing groups or donating groups can be attached that facilitate hole or electron transport. These aromatic or conjugated materials as active semiconducting layer may include small molecules such as rubrene, tetracene, pentacene, diindenoperylene, perylenediimides, tetracyanoquinodimethane, C60, quaterthiophene, α-sexithiophene, α,ω-dihexylsexithiophene, polymers such as polythiophenes (especially poly 3-hexylthiophene), polyfluorene, polydiacetylene, poly 2,5-thienylene vinylene, poly pphenylene vinylene, and all their derivatives. A preferred embodiment includes pentacene and its derivatives, such as TIPS pentacene.

The thickness of the organic semiconductor layer is substantially not relevant to achieve the goal of the invention, a preferred embodiment includes an organic semiconductor layer having a thickness comprised between 5 nm and 50 nm, even more preferably between 10 nm and 20 nm. Alternatively, with semiconductors deposited in liquid phase, the thickness of the semiconductor layer is preferably above 100 nm.

The insulating gate dielectric layer (called in the following either insulating layer or dielectric layer without any difference in meaning) between the floating gate electrode and the organic semiconductor has preferably the following characteristics.

The relationship between the drain current and the various characteristics and applied voltages of the organic transistor is interpreted through conventional semiconductor theory, which reproduces the general trends in organic transistor characteristics $$I_D = \frac{W}{L}\mu_P C_i \left[(V_{GS} - V_{TH})V_{DS} - \frac{V_{DS}^2}{2}\right]$$

from which the saturation current is $$I_D^{sat} = \frac{W}{2L}\mu_P C_i [(V_{GS} - V_{TH})^2]$$

where $C_i$ is the capacitance per unit area of the gate insulator, $\mu_p$ is the charge-carrier mobility, and $V_{TH}$ is the threshold voltage. The drain current depends—among others—on the voltage difference between the control gate electrode and the source electrode.

From this equation, it is clear that several parameters can be tuned in order to obtain significant drain current with low applied voltages. One of those is the capacitance.

The capacitance between the floating gate electrode and the source and drain electrodes is inversely proportional to the thickness of the dielectric or insulating layer, thus the voltage to be applied to the gate is higher the thicker the dielectric layer, in order to control the conductance of the channel. Therefore, in order to reduce the operating voltage of the organic transistor, a first possibility is to reduce the thickness of the dielectric layer.

However, reducing the thickness of the dielectric layer also reduces the resistance between electrodes located at the opposite sides of the insulating or dielectric layer, such as the floating gate and drain and source contacts, which increases the leakage of the transistor and therefore of the undesired currents. Therefore the thickness of the dielectric layer cannot be indefinitely small.

Preferably, the thickness of the dielectric layer is comprised between about 1 nm and about 100 nm.

In another example, the dielectric layer has a capacitance per unit area which is comprised between about 10 nF/cm2 and about 150 nF/cm2 which leads to a high enough current with low voltages. Higher capacitances are suitable as well however the fabrication process of such layer(s) becomes unreliable with a high percentage of layers outside the required specifications.

An important requirement for successfully employing this system of transistors with living cells (especially when targeting in-vivo interfaces) is that the applied static voltages are preferably kept as small as possible to reduce risks of undesired electrochemical processes and enhance sensitivity. In order to fulfill this constraint and to optimize the cell-transistor interface for detecting rapidly varying, low amplitude extracellular electrophysiological signals, the structure of low voltage organic transistor has been redesigned.

In particular, the insulating layer was preferably fabricated with the characteristics above listed, either within a range of thicknesses or capacitance per square unit.

Although a single organic transistor would suffice to measure the signals from the cells indicating their activity, a plurality of organic transistors is used in the system of the invention. Indeed, a plurality of transistors allows a better spatial mapping of the cell's activity location. In other words, having a plurality of transistors allows forming a two-dimensional map of the activity of the cells within the sensing area: indeed in the sensing area a plurality of "portions" of different floating gate electrodes belonging to different transistors is present and thus a detected signal due to the activity of the cells, depending on where it is detected, can be spatially located. Furthermore, as better detailed below, transistors can be used not only to sense signals from cells but to send a stimulus to the cells themselves. In this way the corresponding reaction of the cells to the stimulus can be detected and spatially mapped in a two-dimensional matrix of points (a point for each transistor).

Preferably the sensing area is surrounded by the plurality of transistors which are angularly spaced around the sensing area. All components of the transistors are external to the sensing area, with the exception of the floating gates. The floating gate of each transistor of the plurality extends into the sensing area.

For example, the sensing area, surrounded by a barrier, is wetted by a culture medium where the cells are present. The bottom of the sensing area is covered by a biocompatible layer. This layer is used to be put into contact with the cells. In the layer, openings or apertures are formed to expose the floating gate which is present underneath. Preferably, an aperture for each floating gate is formed in the biocompatible layer so that all the floating gates are exposed to the cells activity. Preferably thus the culture medium is in contact to all first portions of floating gates of the transistors' plurality via the apertures formed in the biocompatible layer.

The size of the apertures is preferably comprised between 4*10-4 mm2 and 8*10-3 mm2.

The small opening lower limit is tailored on the dimension of few, preferably of a single neuronal cell to guarantee a one-to-one coupling with the sensing electrode. The upper limit is to allow the coupling with few cells at the same time.

The apertures form substantially an array, and in turn this outline forms an array of "sensing points" distributed in the sensing area so that each aperture is associated to a floating gate portion and thus to a point of measurement of cells' activity.

The apertures thus are preferably arranged in a two-dimensional array.

Each organic transistor of the plurality, located outside the sensing area, is thus apt to measure the activity of the cells which can be sensed by the exposed area of its floating gate which is in contact with the cells due to the aperture formed in the biocompatible layer. Each aperture defines a sensing point. A 2-D grid of sensing points, each point associated to an aperture and to an organic transistor, is thus formed. Small apertures allow to differentiate the activity of cells which takes place in the neighborhood of a given aperture, that is, small apertures allow to differentiate from which aperture—and thus from which floating gate—the cells activity has been recorded and thus in which position in the 2-D space of the sensing area the activity of the cells took place.

Preferably, the floating gate of each transistors is located within the sensing area in contact to the cells. Ionic charge variations occurring in the close proximity of the aperture of the sensing area located above the floating gate determine a charge separation in the floating gate electrode, leading in turn to a modulation of the charge carrier density inside the channel of the transistor. This charge variation in the floating gate electrode, due to the cells activity, is called "QSENSE".

The working point of each organic transistor is set by means of the control gate electrode forming a control capacitor with the floating gate electrode. Indeed, a second portion of the floating gate electrode of each organic transistor of the plurality forms a capacitor with the corresponding control gate electrode of the same transistor. In fact, the potential VFG of the floating gate electrode depends on the voltage VCG applied to the control gate and the source electrodes, on the voltage VD applied to the drain electrode, to the voltage VS applied to the source electrode, on the capacitances present in the structure, and on the charge Q0 entrapped in the floating gate due to the fabrication process, as described in the following expression:

$$V_{FG} = \frac{c_{CF}}{c_{TOT}} V_{CG} + \frac{c_{DF}}{c_{TOT}} V_D + \frac{c_{SF}}{c_{TOT}} V_S + \frac{Q_{SENSE} + Q_0}{c_{TOT}} \quad (1)$$

where $V_{FG}$ is the voltage of the floating gate electrode.

Considering all the terms as constants, apart from the charge QSENSE (which depends as said from the signals coming from the cells), the field effect modulation can therefore be described in terms of a threshold voltage shift of the device:

$$\Delta V_{TH} = \frac{Q_{SENSE}}{c_{TOT}} \quad (2)$$

being $Q_{SENSE}$ the charge coupled to the sensing area, and $C_{TOT}=C_{CF}+C_{SF}+C_{DF}$ the sum of all the capacitances of the structure (i.e., the control capacitor $C_{CF}$ and the parasitic components due to the superposition between floating gate and the metal contacts lying on the opposite side of the dielectric layer, $C_{SF}$ and $C_{DF}$). The modulation of the threshold voltage through the charge $Q_{SENSE}$ is the mechanism that can be employed for sensing all those chemical and biological reactions that determine a variation of charge onto or in a close proximity of the sensing area. In other words, the threshold voltage depends on $Q_{SENSE}$ which means that the threshold voltage varies according to the cellular activity which can be thus measured by measuring the drain current $I_{DS}$.

The overlapping area defined by said control gate electrode formed above said floating gate is comprised between 9*10-4 cm2 and 2*10-3 cm2. This is to say that the control gate electrode is realized above the floating gate in order to form the capacitor. The area occupied by the gate electrode is comprised within the above mentioned range. This rather small area has been selected in order to obtain the required sensitivity: as shown by equation 2, the variation of Vth due to the charge present in the sensing area is inversely proportional to the capacity of the control gate. Therefore, such a small area allows to obtain relatively high variations in voltage for small changes in charge.

In the specific application targeted in this application, i.e. monitoring of the electrical activity of cells, the charge variation to be sensed by the system is not a quasi-static charge variation but is related to the rapid ionic displacement occurring across the cell membrane that faces the sensing area during an action potential. This small charge variation leads to a charge re-distribution in the floating gate electrode, thus modulating the density of charge carriers inside the channel of the transistor. As a result, an output current variation (i.e. the variations of IDS) is obtained and can be straightforward processed by a dedicated readout circuit. Being the working point of each organic transistor of the system set by means of the control gate electrode, the system does not require an additional or external reference electrode, thus overcoming one of the major drawbacks of MEAs, standard FET-based devices and standard OTFTs. Further, the active part, that is, the transistor area where the transistors are present, is located outside the sensing area. This particular feature, together with the advantages given by the use of organic materials, makes this system an excellent candidate for advanced in-vivo bio-electronic interfaces. The system further also is rather miniaturized and at the same achieves the necessary sensitivity to study the cells' behavior.

Thus each organic transistor of the plurality has two gate electrodes: a first one—the floating gate electrode—used as a sensing point located in the sensing area (a portion of each floating gate is located within the sensing area) to detect the charge variations due to the cells' activity, and a second one—the control gate electrode—to properly bias the organic transistor into the desired working point. The organic transistor can be thus switched on and off as desired.

Therefore, the system of the invention and the method using the plurality of transistors of the invention, due to the construction of each organic transistor of the plurality allows avoiding the presence of an external reference electrode. Generally, these reference electrodes are rather bulky. Furthermore, in case a reference electrode is present, a single reference electrode common to all transistors is to be shared due to the fact that in the sensing area a culture medium is present which is in contact to all floating gate electrodes and thus a polarization due to an external electrode is shared by all floating gate electrodes of all transistors. According to the system and method of the invention, each organic transistor can be properly adjusted via its specific control gate electrode. The threshold voltage of the various transistors can be different due to their fabrication process. However, the source-drain current of each transistor depends on the difference between the control gate voltage and the threshold voltage. It is possible to have the same drain current IDS only if the above mentioned voltage difference is the same for all transistors. This in turn means that it is desirable to select a different control gate voltage for all transistors, so that the difference is kept constant for all transistors also in case of differences in the threshold voltages. The control gate electrode is therefore suitable to apply the correct control gate voltage VGS to the transistor it belongs to, so that the difference is kept substantially identical for all organic transistors of the plurality. Furthermore, the control gate electrodes can be integrated in the same substrate as the remaining organic transistor's parts. Variations on the drain current IDS of each organic transistor due to the cells activity can be measured knowing that the transistors are—from a measurement point of view—all identical among each other.

Furthermore, the construction and design of the insulating layer allows the organic transistors of the plurality to work at very low voltage.

Thus, the system and the method of the invention allow detecting the activity of the living cells. All organic transistors are preferably individually biased by means of the control gate electrode belonging to each transistor at a low voltage. The activity of the cells can be mapped in a two dimensional matrix due to the presence of a plurality of sensing points given by a plurality of portions of a plurality of floating gate electrodes belonging to different transistors which are exposed to the cells' activity within the sensing area at each aperture of the biocompatible layer. Indeed, the portions of the floating gates are located within the sensing area where the cells are cultured or positioned and exposed to the cells due to the apertures. The various "portions" in contact to the cells due to the apertures form substantially an array of sensors whose locations are known and therefore when they detect a signal coming from the cells, also the location(s) of the signal is known. A two-dimensional mapping of the cells' activity is therefore possible, keeping the signals coming from the first portions of the floating gates separated one from the other.

A single transistor of the system including the plurality of transistors forming an array, named Organic Charge-Modulated Field Effect Transistor (OCMFET), is schematically represented in FIG. 1a. Only a portion of the sensing area is shown, where the cells are deposited or cultivated. The transistor is preferably a floating gate thin film transistor OTFT (FIG. 1a), whose working point is set by means of a control capacitor (FIG. 1b). The working point is set by applying appropriate VGS (between control gate electrode and source electrode) and VDS (between drain and source electrodes), till the desired IDS is obtained (see the graph of the IDS vs time on the right of FIG. 1b). The charge fluctuation over the sensing area determines a charge redistribution inside the floating gate electrode, which modulates the charge carriers density inside the channel of the transistor. As a result, a variation of the output current of each transistor, the drain current IDs, is obtained as depicted in the graph on the right of FIG. 1c. The first portion of the floating gate electrode on which cells are cultured is for example exposed, as a direct interface, to the surrounding bio-electro-chemical environment. In particular, ionic charge variations occurring in the close proximity of the sensing area determine a charge separation in the floating gate, leading in turn to a modulation of the charge carrier density inside the channel of the transistor.

The invention according to the first or the second aspect may include any of the following characteristics either alternatively or in combination.

Preferably, the working point of all transistors in the plurality is set substantially identical.

For example, the system may include a comparing element apt to select a plurality of said control voltages, each control voltage being applied to a respective control gate electrode of each of the organic transistors of the plurality, said control voltages being so selected that all organic transistors in the plurality have all a substantially identical drain current when the cells activity is not monitored.

As mentioned, one of the advantages of having each organic transistor of the plurality with a control gate electrode is that the electrodes can be individually biased and their working point can be selected independently. Due to the production process tolerances, all or some transistors may need to be biased with different biasing voltage in order to work with the same passive drain current $I_{DS}$ which means that when there is no measurement of the cells' activity, all the organic transistors of the plurality have substantially the same output current $I_{DS}$. Each organic transistor of the plurality therefore is preferably calibrated and the drain currents output of the various transistors are compared, for example by means of a comparing element, e.g. a circuit element, so that the static output currents of the transistors when not in a monitoring operative state, are very similar.

Preferably, one of said apertures in said biocompatible layer is covered by a piezoelectric material layer, said piezoelectric material layer being deposited above a floating gate of an organic transistor of said plurality, so that said organic transistor is apt to be used as a mechanical stress sensor.

Preferably, one of said apertures in said biocompatible layer is covered by a pyroelectric material layer, said pyroelectric material layer being deposited above a floating gate of an organic transistor of said plurality, so that said organic transistor is apt to be used as a temperature sensor.

For example a polyvinylidene fluoride can be used. In this case a PVDF layer deposited on top of the aperture and thus in contact with a floating gate of a transistor is both a pyro- and piezo-electric material which is used to "transform" the organic transistor in a temperature sensor and in a stress sensor.

Preferably, one of said apertures is covered by a layer of a material which protonize/deprotonize under pH variations, said layer being deposited above a floating gate of an organic transistor of said plurality, so that said organic transistor is apt to be used as a pH sensor.

A protonizing/deprotonizing effect is the reaction of certain material, in particolar of certain insulating material such as oxides, that bind or not with a hidrogen ion depending on the pH of the solution in which they are placed. In other words, protonization is the binding of a hydrogen nucleus H+ to a negative or negatively polarized part of a molecule.

An example of such a protonizing/deprotonizing layer, a layer of halogenated parylene which has been plasma activated can be employed. As parylene, a Parylene C can be used.

If an adequate number of organic transistors is provided, some of the transistors can be used to measure and/or detect additional parameters regarding the cells or the cells' culture. For example, depending on an additional layer that can be positioned between the floating gate and the cells, one or more of the organic transistors can be used as a pH sensor, a temperature sensor or as a stress sensor. In a single system therefore a plurality of parameters can be detected.

Preferably, the superposition between source electrode, drain electrode and floating gate electrode is less than 3% of an area W×L where L is a distance between the drain and the source electrodes and W a width of the source and/or drain electrode.

Preferably, W is comprised between 5 mm and 25 mm and L is comprised between 10 μm and 100 μm.

This area is substantially the channel area of the transistor.

As mentioned, the system and method of the invention preferably need to be able to detect charge variations at high operating frequencies. In order to achieve this, the system has been designed in order to minimize parasitic capacitance that detrimentally contributes to determine the overall capacity of the transistor. Essentially, the superposition between source, drain and floating gate electrodes has been minimized, for example employing a self-alignment procedure.

The potential of this system and method in cell activity monitoring is correlated to its capability of detecting very small amounts of charge (less than 1 pC) at relatively high frequency (up to 1 kHz).

Preferably, the system and the method include in the plurality at least eight organic transistors.

This number of transistors allows having a rough 2-dimensional map of the cells' activity.

Preferably, the system includes a substrate on which said floating gate electrode is formed, said substrate including a flexible plastic material.

The substrate on which the floating gate electrode of each organic transistor is realized is preferably a plastic flexible substrate, which can be later deformed and adapted to every generic surface on which the system should be assembled. This allows a great flexibility in the use of the system in different applications.

More preferably, said substrate is at least partially transparent to visible radiation.

The transparent substrate is preferred due to the fact that to check the cell culture state or cell positioning, transmission optical microscopy is routinely used. Further, a transparent substrate can be useful in the lithographic process.

Advantageously, said first portion of floating gate of each organic transistor includes an area having the largest dimension comprised between 1 μm and 100 μm.

The floating gate has a first portion which is part of the sensing area, i.e. the floating gate includes a portion of the sensing area where the cells are deposited. This area is preferably bigger than the cells itself and small enough to obtain a given sensitivity of the location of the cells' activity.

Preferably, said floating gate electrode is made of a biocompatible material.

Being a portion of the floating gate in contact with the cells through the aperture in the sensing area, it is preferred that the floating gate itself is realized as a suitable substrate on which cells can grow. For example, the floating gate could be covered by layers of proteins, polymer or amino-acids suitable to culture cells, such as laminin, polylysine, eumelanin, etc.

Preferably, said biocompatible layer is realized in Parylene C, polyimide, metal oxide or any combination thereof.

More preferably, said floating gate electrode is realized in Ti, TiO2, TiN, indium tin oxide (ITO) or other transparent conductive oxides, conductive polymer, and any combination thereof.

In a preferred embodiment, said insulating layer includes a metal oxide layer having a first thickness comprised between about 0 nm and about 20 nm and a first relative permittivity $\varepsilon 1$, and a dielectric polymer layer having a second thickness comprised between about 0 nm and about 50 nm and a second relative permittivity $\varepsilon 2$ and forming an interface with said organic semiconductor, wherein said first and second thicknesses are not both equal to zero.

Considering a metal oxide film as a possible insulating layer, the film is usually characterized by a very low vertical resistivity, which gives rise to very high leakage currents (currents that flows from the source electrode to the gate electrode). Moreover, the oxide film is usually characterized by a very high concentration of surface defects that normally increase charge carriers trapping, thus limiting mobility and increasing the organic transistor threshold voltage.

Indeed an additional goal of the present invention is to render available an organic transistor which is relatively easy to fabricate and which is highly reproducible at low cost. In addition, it is desired that the organic transistor of the invention can be realized on flexible substrates.

Applicant has also tested the possibility to deposit as insulating layer a layer of dielectric polymer, for example parylene C, as better detailed below, but in order to achieve good insulating properties, the thickness of the polymeric layer has to be relatively high.

Applicant proposes an alternative fabrication procedure for obtaining an ultra-low voltage transistor that is simple, low-cost, and, most of all, very easily up-scalable to industrial size with a very high yield. In a preferred embodiment, these results have been achieved by employing a unique combination of different dielectric materials as insulating layer.

According to the above, the organic transistor of the invention includes, between the organic semiconductor layer and the floating gate electrode, an insulating layer which is "ultrathin" (the dimension of which will be better defined below), but at the same time, ensures a good electrical insulation and rigidity and can be fabricated also on plastic and more in general, flexible substrates.

This insulating layer is preferably a combination of two layers: a first layer which includes a metal oxide, called in the rest of this description a metal oxide layer, and a second layer which includes a dielectric polymer, in the following called dielectric polymer layer. This second layer has to form the interface with the organic semiconductor, i.e. the polymer dielectric layer is in contact with the organic semiconductor above described.

The metal oxide layer is preferably the native oxide of the floating gate electrode, that is, it is spontaneously formed on top of the floating gate electrode.

The thickness $T_1$ of the metal oxide layer is comprised between $0 < T_1 \leq 20$ nm, preferably between $0 < T_1 \leq 10$ nm, more preferably 5 nm$\leq T_1 \leq$10 nm.

The layer may include preferably metal oxide of the general formula M1xOz, or a complex mixed metal oxide of the formula M2xM3yOz wherein all of M1-M3 are independently selected ions of metallic elements.

A metallic element refers to the identity of the element in any chemical form, i.e. a metallic element is an element classified as metallic which can be in the form of an elemental metal or can be in the form of a salt or complex of a metal. A metallic element in metallic form refers to the non-oxidized metal, whereas a metallic element in salt or complex form refers to the metal in chemical combination with other elements. A "metal oxide" includes various species wherein the metal ion, although comprising an identical metallic element, is in a different oxidation state in distinct species, and thus is composed with different stoichiometry.

Preferred metals are for example Aluminum, Gallium, Indium, Zinc, Titanium, Iridium. In the described example, the metal oxide layer includes alumina (aluminum oxide).

The thickness T2 of the dielectric polymer layer is comprised between $0 < T2 \leq 50$ nm, preferably between $10 \leq T2 \leq 30$ nm, more preferably 15 nm$\leq T2 \leq$25 nm.

The second dielectric layer includes a dielectric polymer. Preferably, this polymer is deposited via chemical vapor deposition (CVD). More preferably, the dielectric polymer includes poly(p-xylylene), also known as parylene N of repeating unit

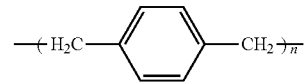

and its derivatives.

More preferably, the second layer includes halogenated parylene, even more preferably parylene C having repeating unit:

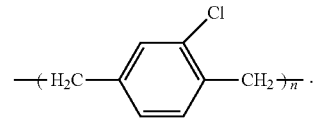

Other possible materials can be for example Poly(methyl methacrylate) (PMMA), Polyvinyl alcohol (PVA) or Polyvinylpyrrolidone (PVP), PolyStyrene (PS) and undoped PolyPyrrole (PPy).

More preferably, said first and second relative permittivity satisfy the following equation $|\varepsilon_1-\varepsilon_2|\leq 10.$ The vacuum permittivity ε0 (also called permittivity of free space or the dielectric constant) has the following value $$\varepsilon_0 \stackrel{def}{=} \frac{1}{c_0^2\mu_0} = \frac{1}{35950207149.4727056}\frac{F}{\pi\,m} \approx 8.8541878176\ldots \times 10^{-12}\frac{F}{m}.$$

From the above, the relative permittivity εr (also called dielectric constant of the material) of a material is defined as the ratio between its permittivity and the vaccum permittivity:

$\varepsilon=\varepsilon_r\varepsilon_0=(1+\chi)\varepsilon_0.$

An additional characteristic of the transistor of the invention is thus the following: called ε1 the relative permittivity of the material realizing the first dielectric metal oxide layer and ε2 the relative permittivity of the material realizing the second dieletric polymer layer, the two permittivities preferably satisfy the following equation:

$|\varepsilon_1-\varepsilon_2|\leq 10,$ more preferably $|\varepsilon_1-\varepsilon_2|<5.$ The thickness T1+T2 of the dielectric layer is still rather thin in order—as already explained—to increase the capacitance of the whole film, but also a very low leakage is achieved. This effect is obtained thanks to the combination of the properties of the metal oxide layer and of the polymer layer. In reality, the two layers are not completely separated: during the deposition of the polymer layer, the polymer itself might intermingle between the metal oxide molecules, interposing between them to form a sort of "unitary layer".

It is very important to notice that the charge transport in OFETs occurs within 1-2 nanometers of the semiconductor/dielectric interface. Hence the properties of this buried interface, such as its roughness, defect and trap density, and orientation and interchain packing of the OFET molecules or macromolecules, is central to the device performance. Applicants have realized that a good interface between the semiconductor and the dielectric layer is therefore important to obtain organic transistor having a low operating voltage: a non-optimal interface may lower the drain current of several orders of magnitude in comparison with identical transistors having a better interface. In addition, having a good interface between the dielectric layer and the organic semiconductor lowers the threshold voltage above which the transistor starts working. Applicants have noticed that a film of metal oxide as dielectric layer does not create an optimal interface with the organic semiconductor. The same result is usually achieved when a double layer is formed where the permittivity of the two materials is very different one from the other.

As a matter of fact, obtaining a high gate dielectric capacitance and keeping the leakage current density very low are necessary but not sufficient conditions in order to achieve very low operational voltages. Minimization of charge carriers trapping, which usually takes place at the interface between the gate dielectric and the organic semiconductor, plays an as much essential role in determining the operating voltages and the transport properties of the final device. Such defective sites cause a reduction of the semiconductor mobility but can also dramatically affect other electrical parameters, in particular threshold voltage and, as a consequence, the working voltages of the device. For these reasons, to obtain an ultra-low voltage transistor, a full control of all properties of the insulating dielectric layers, not only thickness, is preferred.

Advantageously, said dielectric polymer layer includes poly(p-xylylene) and/or its derivatives and more preferably said dielectric polymer layer includes halogenated parylene.

It is worth noticing that according to the method of the invention, a plurality of information regarding the cells' can be collected using a single system. Indeed, covering some of the apertures realized in the sensing area which exposes the underneath floating gate with layers of selected proper materials, some of the organic transistors of the system can be used to detect properties like the temperature, stress, pH and the like of the cells to obtain a complete characterization of the cells themselves.

According to a third aspect, the invention relates to a method to send an electrical stimulus to a plurality of living cells deposited on a system realized according to the first aspect of the invention said method including the steps of
    sending a stimulus to said cells by means of said floating electrode of one transistor of said plurality or by means of said control gate electrode of one transistor of said plurality.

In a preferred embodiment, said method includes:
    detecting the response of said cells to said stimulus by means of the first portions of the floating gates of the remaining transistor of said plurality.

Further, the invention also relates to the method to stimulate one or more cells and preferably also to sense or detect the response to the stimulus. This can be achieved sending a voltage stimulus by means of either the floating gate electrode or the control gate electrode of one of the transistor of the plurality in a defined location (i.e. the geometrical position of such a control or floating gate). The spatial distribution of the response of the cells to such a stimulus can be detected using the floating gates, in other words the parts of the floating gates which are within the sensing area, in order to have a two-dimensional map of the response.

In a preferred embodiment the impulse is sent by means of one of the floating gates, forming a back contact on top of the floating gate.

Due to the array structure of the exposed parts of the floating gates in the sensing area (uncovered portions of the floating gates form an array and are exposed to the cells due to the apertures), the spatial position in which the signal is sent is determined and selected. A stimulation of certain parts of the cells can take place—

For example, the impulses have approximately an amplitude between 1 mV and 1V, a time duration comprised between 10 μs and 1 ms and preferably the total number of impulses is one each 2-5 seconds for approximately 5-10 minutes in total. Any other impulse can be used as well, depending on the type of cells and experiment.

BRIEF DESCRIPTION OF THE DRAWINGS

FIG. 1a shows a cross section of a single transistor. FIG. 1b, shows the method to set the static drain current of a single transistor by applying appropriate $V_{GS}$ (between control gate electrode and source electrode) and $V_{DS}$ (between drain electrode and source electrode). FIG. 1c shows the charge fluctuation due to cells activity over the sensing area determines a charge re-distribution inside the floating gate, which modulates the charge carriers density inside the channel of the transistor. As a result, a variation of the output current, that is the drain current, is obtained;

FIG. 2 is a schematic perspective view of a single organic transistor of the system;

FIG. 3 shows four graphs of the characteristics of an ultra-low voltage transistor included in the system of the invention right after the fabrication (the two graphs at left) and after 10 days inside an incubator (the two graphs at right);

FIG. 4 is a top view of the system of the invention including 16 transistors on a substrate; in the center of the substrate, the first portions of the floating gates used as sensing pads are surrounded by a glass ring that allows confining the culture medium with the cells. The glass ring is an embodiment of a mechanical barrier confining the culture medium and the cells;

FIG. 5 is a top view of an embodiment of the complete system of the invention. The readout electronics to monitor cells' activity in inserted onto a multichannel Systems ground plate;

FIG. 6 is a graph of the gain vs frequency relationship for a single transistor of the plurality employed for the measurements with cells;

FIG. 7 is a side view in section of a single transistor of the plurality;

FIGS. 7a and 7b are enlarged top view of details of the side view of FIG. 7;

FIG. 8 is a simplified top view of a single transistor of the plurality with some portions enlarged;

FIG. 11a is a schematic representation of an impulse signals used in the systems of FIGS. 10a-10b and 11;

FIG. 12a is a magnification of the sensing area in which a confluent culture of rat cardiomyocytes (8 DIV) is adhering on the surface, while FIG. 12b shows a Cardiomyocytes culture fixed after a recording session and immunostained for the sarcomeric protein Tropomyosin;

FIG. 14 is a graph showing the spontaneous activity of a rat cardiomyocytes culture (8 DIV) maintained at 37° C. measured with the system of the invention;

FIG. 15 are two raster plots obtained measuring the drain current vs time by the system of the invention representing the thermal modulation of the spontaneous activity of the culture. The temperature was incremented from 35° C. to 40° C. (left plot) and decreased from 40° C. to 35° C. (right plot) causing a consistent variation of the beating frequency;

FIG. 16 is a graph obtained measuring the drain current vs time by the system of the invention showing the chemical tuning of the culture's activity. The spontaneous activity was accelerated by means of the addition of 100 μM of Norepinephrine and then suppressed with 100 μM of Verapamil;

FIG. 17 shows the beating frequency modulation (statistics on 5 transistors—average and standard deviation): spike-count on 4 min of basal (129±4.6), NE-mediated (280±28.6) and VER-mediated activity (15±1.9);

FIG. 18, represents the signal propagation reconstruction in a device with multiple recording sites: colored and black dots represents, respectively, transistors that recorded signals and "silent" transistors (left); and a raster plot of the spontaneous activity of the "colored" channels indicating a propagation of the signal from site 14 to site 41 (right)

DETAILED DESCRIPTION OF THE PREFERRED EMBODIMENTS

Figure 1A:
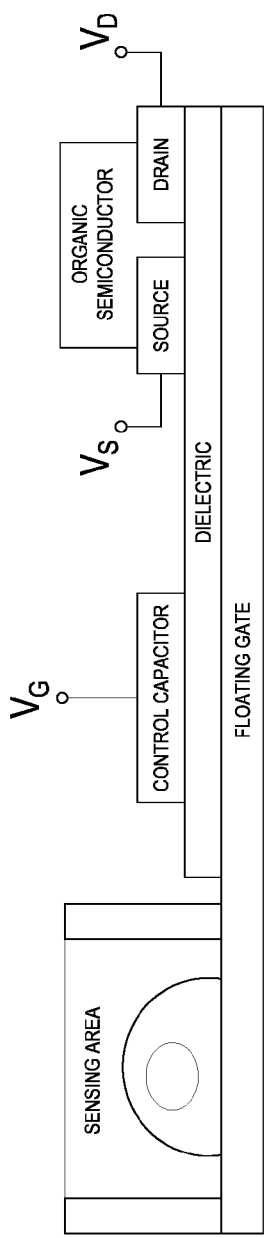
FIGS. 1a-1c are schematic representations of a working principle of one of the transistor of the system.
Figure 1B:
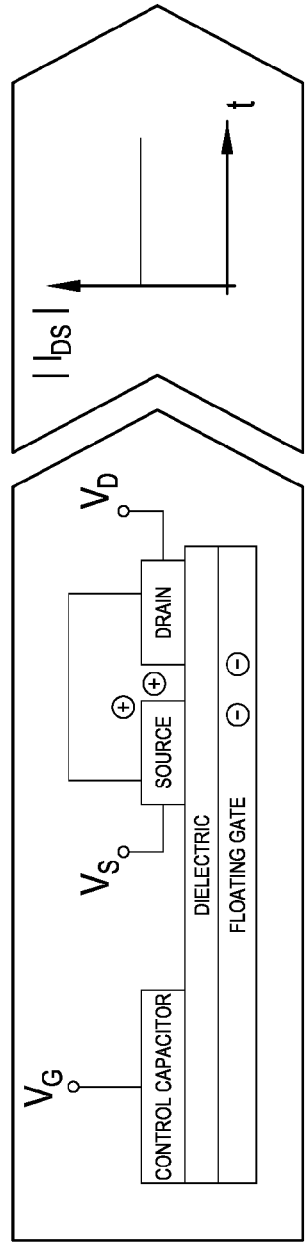
Figure 1C:
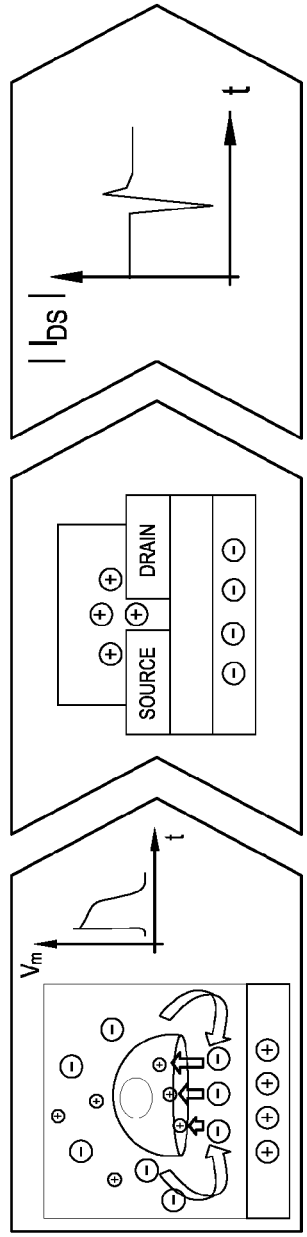
Figure 9:
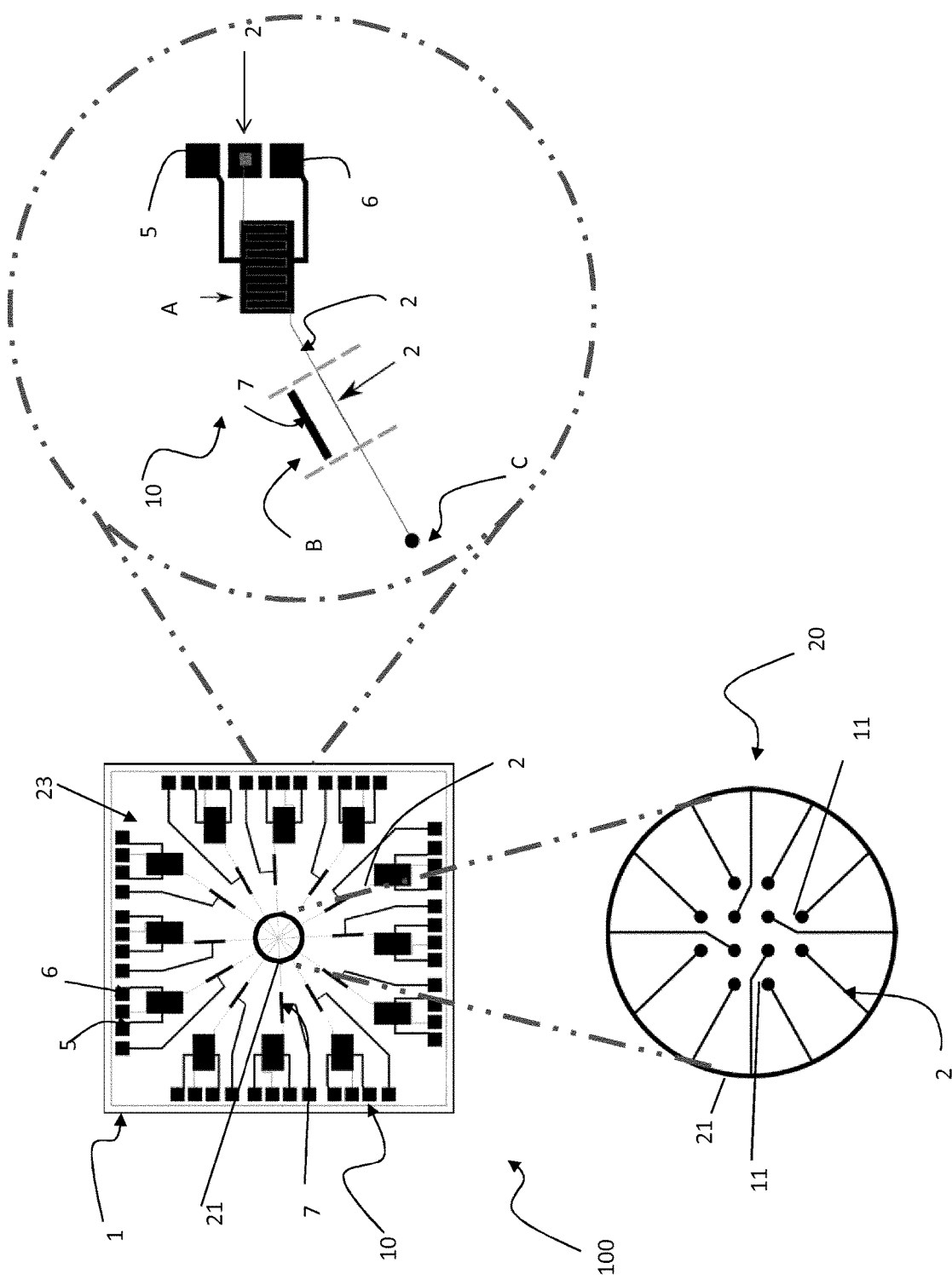
FIG. 9 is a simplified top view of the system of the invention with some portions enlarged.

With initial reference to FIGS. 2, 7 and 8 an organic transistor according to the present invention is globally indicated with reference numeral 10. The organic transistor 10 is part of a system 100 including a plurality of transistors 10 as depicted in FIGS. 9 and 4.

In the appended drawings, the organic transistor 10 is a low voltage OFET (or OTFT) having a bottom gate top contact configuration, however the teaching of the invention can be applied to other transistors and/or configurations as well.

The OFET 10 is realized on a substrate 1 which can be any substrate, preferably it is a flexible plastic substrate. In the preferred embodiments, the substrate 1 includes polyethylene terephthalate (PET), which is transparent and flexible, or poly (4,4'-oxydiphenylene-pyromellitimide) (commercially known as Kapton).

The OFET 10 includes a control gate 7, a drain 5 and a source 6 electrodes. The material in which the electrodes are realized can be any known material suitable for the purpose and known in the specific technical field, for example gold, aluminum, Poly(3,4-ethylenedioxythiophene) (PEDOT), PEDOT:PSS, silver. Preferably, the electrodes 5-7 are realized in Gold. Further, the OFET 10 includes a floating gate 2 preferably realized in titanium Ti.

On top of the floating gate electrode 2, the dielectric or insulating layer is realized. According to an embodiment of the invention, the dielectric or insulating layer is realized using a combination of a metal oxide layer 3 and a dielectric polymer layer 4, one on top of the other. However, a single dielectric layer can be used as well.

In this embodiment, advantageously, the metal oxide layer 3 is realized in $TiO_2$ using the oxidation of the titanium layer deposited to create the floating gate electrode 2. Therefore, this first dielectric layer can be obtained using a very simple process step. This oxidation step can be used also with other metals in addition to Aluminum or Titanium.

In this way, a very thin metal oxide film 3 has been fabricated at the top of the floating gate electrode 2.

At the top of the metal oxide layer 3, an additional layer made of insulating polymer 4 is realized. This double layer configuration allows on one hand shielding surface defects of the metal oxide layer, thus strongly limiting charge trapping, on the other hand to dramatically increase vertical resistivity thus almost cancelling current leakage through the gate dielectric.

As an example, the organic transistor 10 of the invention includes a polymer layer 4 comprising a biocompatible, insulating material called Parylene C.

The Parylene C layer is deposited, preferably by Chemical Vapor Deposition. The final insulating film thickness is still thin enough to allow the OFETs 10 working at very low voltages.

At the top of this structure, source and drain and control gate electrodes 5, 6, 7 can be fabricated using different patterning techniques (photolithography, metal deposition through shadow masks, inkjet printing etc.) and a thin film 8 of a proper organic semiconductor can be deposited in contact to source and drain electrodes 5, 6 in order to have the final OFET 10 completed.

The semiconductor layer 8 can be of any type known in the art for this specific application. The semiconductor can be deposited using different semiconductor deposited, for example thermal vapor deposition (for example in case of pentacene), drop casting (for example in case of pentacene TIPS) and spin coating (for example Polyera N1400).

Two preferred embodiments of the transistor configurations are the following: a first one as depicted in the figures where the floating gate electrode 2 is at the bottom (on the substrate 1) on which the insulating layer 3,4 is fabricated and then in turn on top of it the source/drain electrodes 5, 6 are patterned. Further, the organic semiconductor 8 is located between (and also partially on top) of the source and drain electrodes 5, 6.

Alternatively, the organic semiconductor can be deposited onto the insulating layer and the source and drain electrodes can be patterned onto the organic semiconductor (configuration not shown in the appended drawings).

The transistor 10 can be divided in three zones (see for example FIGS. 7 and 8). A first zone A includes the source and drain electrodes 5, 6 stacked above the floating gate electrode 2. In this zone, a sandwich structure including at the bottom the floating gate electrode 2, covered by the dielectric layer 3, 4, on top of which the source and drain electrodes 5, 6 are formed, in turn covered by the organic semiconductor 8 is formed. In a second zone B, the control gate electrode 7 is formed onto the dielectric or insulating layer 3, 4. The control gate electrode 7 forms a capacitor Cap (see the enlarged inset of FIG. 8), one element of the capacitor being the control gate electrode 7 itself and a second element the floating gate electrode 2. In this zone B, a sandwich structure between the floating gate electrode 2 at the bottom, covered by the insulating layer 3, 4 and on top the control gate 7 is formed. The area covered by the control gate electrode 7, that is the area of overlapping between the control gate electrode and the floating gate is relatively small, that is comprised between $9*10^{-4}$ cm$^2$ and $2*10^{-3}$ cm$^2$. Further, a third zone C where a portion of the floating gate electrode 2 is exposed, not covered by the insulating layer 3, 4, or covered only partly by it, is present. In this zone C, the floating gate electrode 2 includes a first portion which forms the sensing element of the organic transistor 10. This first portion is called in the following sensing pad 11.

The portion of the floating gate electrode 2 forming a capacitor Cap together with the control gate electrode 7 is called second portion of the floating gate electrode 2 (zone B). A dimension of this second portion, which is the bottom contact (floating gate electrode) of the capacitor formed with the control gate electrode, can be for example of 12 mm×0.15 mm. In FIG. 8, the capacitor formed by the floating gate electrode second portion and the control gate electrode is enlarged in the quadratic inlet.

Preferably, the sensing pad 11 has a dimension (such as a diameter or a diagonal depending on its shape) comprised between 10 μm and 100 μm.

In a preferred embodiment, the floating gate electrode 2 has an interdigitated configuration, as visible in FIGS. 2 and 8, and preferably the width/length ratio of the so formed interdigitated channel is comprised between 10 and 30.

With now reference to FIG. 9 and FIG. 4, the system 100 of the invention to monitor cells' activity includes a plurality of transistors 10, all formed on the same substrate 1. Preferably, the plurality of transistors includes at least eight transistors 10 in a star configuration. The transistors 10 are preferably identical one to the other, for example preferably fabricated preferably using the same materials and the same process, however due to the fabrication tolerances, their threshold voltages can be different one from the other.

The transistors 10 are so arranged that the sensing pads 11 of the floating gates 2 are located one close to the other in a form of array, as visible in the enlarged detail of FIG. 9. The distance between two different sensing pads 11 of two different floating gate electrodes 2 belonging to two different transistors 10 of the plurality is preferably comprised between 100 μm and 200 μm.

The sensing pads 11 are located relatively "far" from the transistors 10 and close one to the others. In this way, the sensing pads are concentrated in a relatively small area. This area is covered by a biocompatible layer 4a, that is, the floating electrodes, in their portion extending away from the transistors 10, is covered by a layer which is biocompatible and on which the cells are deposited.

The system 100 is divided in two parts by a barrier 21, for example a mechanical impermeable "wall". The wall 21 surrounds an area which is called sensing area 20. The area outside the sensing area is called transistor area 23 because in this area the transistors 10 are located. The organic transistors 10 are preferably angularly spaced around the wall 21, that is, taking the center of the sensing area as a reference point, the transistors are located at different angles around it, outside the wall 21. The transistors 10 "surround" the wall 21.

Inside the area delimited by the wall 21, called the sensing area 20 where the cells are present, the biocompatible layer 4a, which in some embodiments can coincide with the insulating layer 4 (see for example the embodiment in FIG. 7 where the biocompatible layer is the insulating layer 4, while in FIGS. 11 and 10b the biocompatible layer is a different layer 4a), which is pierced so as to form a plurality of apertures 24 (see FIGS. 7 and 7b). The apertures 24 can be formed for example using a standard photoresist technique and are as deep as the biocompatible later 4a so that the layer underneath become visible. The biocompatible layer is deposited over a substrate 1 and the floating gates 2 which are extending from their respective organic transistors 10. The apertures are formed at the floating gates, that is, the apertures 24 are realized so that a portion of the floating gate 2 of the transistors 10, portion corresponding to the sensing pads, is exposed to the cells and is in contact to the same. The floating gate directly can be in contact with the cells, or the native oxide which forms on top of the floating gate (see layer 3 of oxide). In each aperture 24, a sensing pad 11 is visible, so that the portion of the floating gate 2 visible from the aperture is in contact with the cells. In FIG. 9, the apertures 24 coincides with the sizes of the sensing pad 11 and therefore are not visible.

The transistors 10 located in the transistor area 23 therefore stretches with their floating gates 2 into the sensing area 21 and a portion of the floating gates (sensing pad 11) is in contact with the cells due to the apertures 24 which allows the cells to be in contact directly to the floating gates.

The plurality of sensing pads 11 defines an array of sensing points. In the sensing area 20, the cells are positioned or cultivated in a suitable medium, which is preferably liquid. The barrier 21 therefore avoids any contact between the liquid and the electronic circuitry of the system 100. Any geometrical configuration of the barrier or wall 21 is included in the present invention.

The system is connected to a multichannel system acquisition board (not shown) to detect the output drain current IDS, and its variations, of each transistor 10 of the plurality.

Due to the small size of the control gate and to the material used, the sensitivity of the organic transistor is high enough to detect the cells' activity. In addition, due to the array formation of the sensing pad, a mapping between the cells activity and a 2-D positioning of where the activity has taken place is possible.

Example

Each transistor 10 is fabricated on a 175 μm thick polyethylene terephthalate (PET) substrate 1. At first, a metallic layer (Al or Ti) was thermally evaporated onto the substrate and patterned by means of a standard photolithographic process. This patterned metallic film acts as the floating gates 2 in the final transistor architecture. In particular, the terminal sensing pads 11 of the floating gates 2 have a diameter ranging from 50 to 150 μm. An UV-Ozone treatment was subsequently performed in order to enhance the growth of the superficial native oxide layer (layer 3, few nanometers thick). After that, 30-50 nm of Parylene C (Specialty Coating Systems, layer 4) were deposited onto the entire substrate. A gold layer was then evaporated and patterned using a self-alignment process as described in Lai, S., Cosseddu, P., Gazzadi, G. C., Barbaro, M., Bonfiglio, A. Towards high frequency performances of ultra-low voltage OTFTs: Combining self-alignment and hybrid, nanosized dielectrics. *Organic Electronics* 14, 754-761 (2013), to obtain the drain, source, and control gate contacts 5, 6 and 7. The obtained self-aligned low-voltage transistors 10 have a W/L (channel Width/channels Length) ratio of about 650. A thick layer of photoresist was then deposited and photolithographed in order to expose only a portion of the pads and protect the rest of the surface. Afterwards, the Parylene C layer was etched from the floating gate pads by means of a plasma oxygen exposure in order to form apertures 24. After the photoresist removal, 2 μl of a solution of 6,13-Bis (triisopropylsilylethynyl)pentacene (TIPS Pentacene, Sigma Aldrich) in toluene (0.5 wt %) were drop casted directly over the channel of the transistors (organic semiconductor 8). Finally, a glass ring (1.5 cm in diameter) was glued onto the substrate with a thin rim of polydimethylsiloxane (PDMS) in order to delimit the cell culture region, forming barrier 21, from the transistor area 23. A careful cleaning of the chip surface with ethanol, acetone and deionized water preceded every step of the process.

Experimental Setup

The experimental setup includes a multichannel (16 channels) dedicated readout and conditioning electronic. Each channel comprises three main blocks: a first inverting I/V converter with a 1 MΩ feedback resistor, a 2nd order high pass Butterworth filter with a cut-off frequency of 150 Hz, a 3rd order low pass Butterworth filter with a cut-off frequency of 1.3 kHz. The polarization of the takes place by means of an adjustable biasing circuit for each of the OCMFETs polarization (VDS=VGS=about −1 V for all the reported measurements, with small variations from one transistor to the other). The total voltage gain of the circuit is 110. The realized custom circuit is connected to a Multichannel Systems acquisition board for A/D conversion, acquisition and storage. All the measurement sessions were carried out inside a Faraday cage in order to minimize the electrical environmental noise on the system.

FIGS. 4 and 5 represent two pictures of the system 100 and of the system 100 coupled with the multichannel system and electronics of the invention, respectively. The system 100 includes eight identical transistors 10, which are fabricated on a plastic substrate, having a global size of 50×50 mm to ensure compatibility with standard Multi Channels Systems ground plates. Furthermore, a multichannel readout circuit was specifically designed and realized in order to perform the conditioning of the signals coming from the sensors.

In order to check the stability of the organic semiconductor layer 8, in FIG. 3 both output and input characteristics are shown for a single ultralow-voltage organic transistor 10 realized as above detailed in the example right after its fabrication (left) and after 10 days inside an incubator at 37° C. and 95% of humidity (right). As it can be noticed, the current shows a certain degradation (as the active device area has not been encapsulated), but the transistor behavior is fully preserved.

The system 100 works and monitors cells' activity according to the method of the invention.

Each organic transistor 10 is set into a working point operating the control gate electrode 7, that is according to the voltage at the control gate electrode $V_{GS}$ (in this case between control gate and source electrodes; in the drawings the voltage applied at the control gate is identified as $V_{CG}$, the voltage at the drain electrode $V_D$ and the voltage at the source electrode $V_S$).

All organic transistors 10 preferably undergo a calibration step so that the output drain currents $I_{DS}$ of all transistors are the same (or substantially the same). The voltage $V_{GS}$ (voltage between the control gate and the source) of each transistor is set accordingly, i.e. it is tuned so that the $I_{DS}$ currents of all transistors 10 of the plurality of the system 100 are substantially the same.

The system 100 in order to be used to perform cell activity monitoring has preferably the capability of detecting very small amounts of charge (less than 1 pC) in a frequency range up to 1 kHz. Therefore, in order to optimize the frequency response of the organic transistors 10, a self-aligned structure, as described above in the fabrication example, has been employed that allows obtaining a reduction of the parasitic capacitances, due to the reduction of the overlapping area between source and drain electrodes with the underneath floating gate 2. Preferably this overlapping is below 3%. In other words the source and drain electrodes 5, 6 define a channel area W×L (where L is the distance between the source and drain electrodes and W their width), and preferably the superposition between this area and the floating gate electrode 2 is below 3% of the area itself. The ability of each organic transistor 10 of the system 100 to record relatively high frequency signals is shown in FIG. 6, where a graph of the amplification vs the frequency is depicted. The organic transistor 10 is able to amplify signals at frequencies up to 1 kHz, a frequency that is higher than the typical frequency range of signals from electrogenic cells (both cardiac and neuronal cells).

Figure 12A:
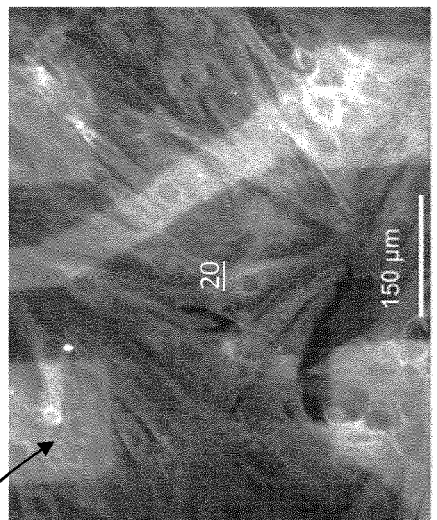
FIGS. 12a and 12b are two photographs of the sensing area of the system of the invention to assess biocompatibility.
Figure 12B:
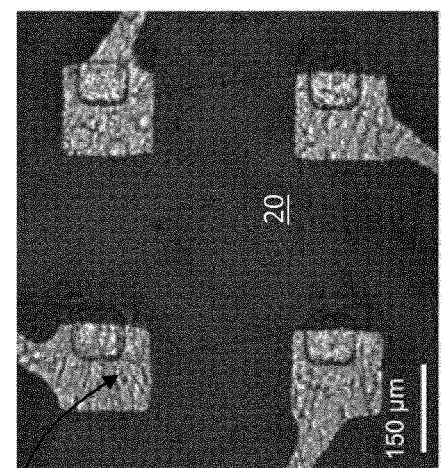

Since the transistor 10 and the system 100 have been fabricated with materials that are intrinsically biocompatible, the biocompatibility of the whole system 100 has been tested. FIGS. 12a and 12b represent two enlarged views of the sensing pads 11 of the system 100. On these pads 11, cells, in this example cardiac cells, have been cultured within a culture medium. As it can be observed in FIGS. 12a and 12b, cardiac cells covering the surface of the sensing pads 11 appear well adherent and well differentiated.

In a test, not depicted, the biocompatibility of system 100 was demonstrated by coupling neuronal cultures into the sensing area 20. Such networks remained in healthy conditions for more than 3 weeks, demonstrating the suitability of the system 100 to long term in-vitro applications.

Figure 13:
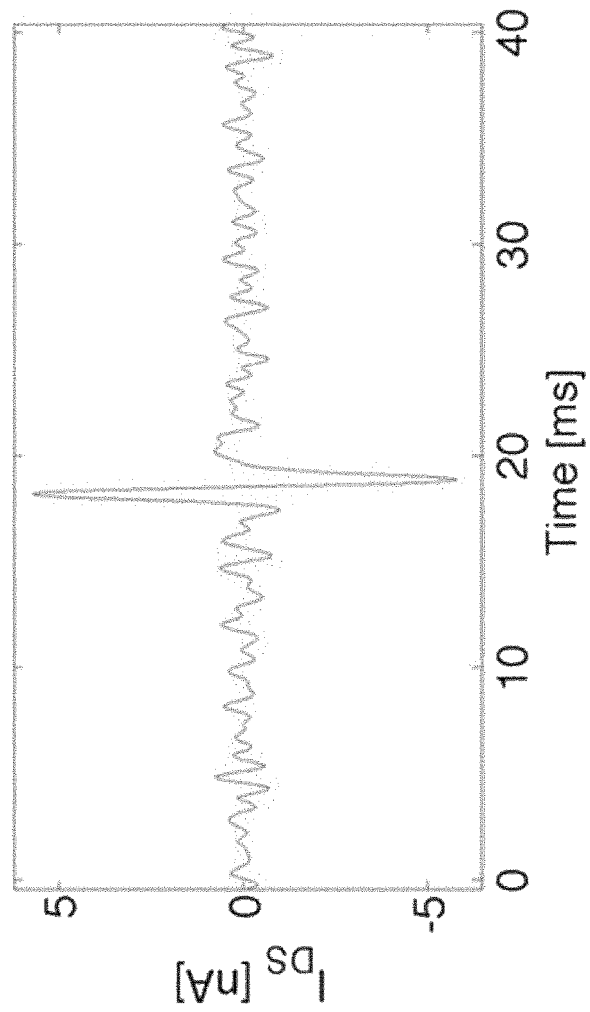
FIG. 13 is a graph representing a single signal measured with the system of the invention. The fast ionic displacement during the early phase of the intracellular cardiac Action Potential (AP) elicits an increase followed by a decrease of the drain current of the transistor. The shape and the duration are coherent with the sensing of the events occurring during the upstroke of the intracellular AP.

In order to prove the ability of the system 100 to record signals generated by living cells, the system 100 has been tested using primary cultures of cardiomyocytes from rat embryos (embryonic day 18), which develop in culture, in a few days, spontaneous and continuous mechano-electrical activity with a beat rate of 0.4 Hz-4 Hz. The system 100 was able to detect the occurrence of the signals (similarly to what MEA-based devices do), the beat rate and its rapid changing related to pharmacological modulations, obtained by applying both positive and negative chronotropic compounds (according to the method described in Simpson, P. Stimulation of hypertrophy of cultured neonatal rat heart cells through an alpha 1-adrenergic receptor and induction of beating through an alpha 1- and beta 1-adrenergic receptor interaction. Evidence for independent regulation of growth and beating. Circ. Res. 56, 884-894 (1985); Yonemochi, H., Saikawa, T., Takakura, T., Ito, S., Takaki, R. Effects of calcium antagonist on β-receptors of cultured cardiac myocytes isolated from neonatal rat ventricle. Circulation 81, 1401-1408 (1990)). In FIG. 13 an example of extracellular action potentials measured, with an organic transistor 10 is shown. Considering a p-type organic transistor and a first inverting stage of the readout electronics, the shape of the single signal shown in FIG. 13 is consistent with the expected current fluctuation caused by the ionic charge displacement in the early phase of the cardiac action potential. The drain current $I_{DS}$ fluctuation is driven by the fast movement of Na+ ions occurring at the very beginning of the intracellular action potential.

Systematic measurements by recording the spontaneous electrophysiological activity of rat cardiomyocytes (8 Days InVitro—DIV) by means of the system 100 (FIG. 14) have been performed.

To further confirm the recording capabilities of the developed system 100, the cell activity has been modulated by slowly varying the temperature of the culture's medium. The control temperature of the thermostat, in contact with the cell plate, has been changed from 35° C. to 40° C. and back. As expected, and shown in FIG. 15, the culture's beating frequency varied consistently with the temperature variations, just comparing the two figures in FIG. 15.

Finally, to ultimately prove that the recorded signals were generated by the cardiomyocyte cells, after several recordings made in physiological conditions (i.e. at 37° C. in a standard culture medium and a controlled atmosphere), the spontaneous activity of the cardiomyocytes' culture was pharmacologically manipulated by administering 100 μM of Norepinephrine (a specific cardiostimulant that acts on β-adrenergic receptors), and then a high-dose (100 μM) of Verapamil (a calcium blocker specific to the L-type calcium channel that acts as a cardio-relaxant). As expected, the system 100 recordings showed modulations of cellular activity as reported in FIG. 16, where it is clear the change in the activity following the change in the recorded current. All the measurements relative to the pharmacological modulation of the electrical activity were performed while maintaining the culture at constant temperature (37° C.) and the same reliable results were obtained in five recording devices simultaneously.

With this array configuration of organic transistors 10 in the system 100, it was possible to estimate the propagation speed of the electrical signal (around 0.4 m/s, in agreement with values measured by means of other techniques, such as for example Darrow, B. J., Fast, V. G., Kléber, A. G., Beyer, E. C., Saffitz, J. E. Increased Conduction Velocity and Enhanced Connexin Expression in Dibutyryl cAMP-Treated Cultured Cardiac Myocytes. Circ. Res. 79, 174-183 (1996)).

Measurements performed with several transistors 10 showed $I_{DS}$ variations ranging from hundreds of pA to few nA. Considering an average $I_{DS}$ variation of 1 nA and representative values of the electronic parameters of the transistor (a trans-conductance $g_m$ of 300 pA/mV and the sum of the capacitances $C_{TOT}$ of 100 pF), using the OCM-FET's equations, a corresponding charge variation of ~0.3 pC has been estimated.

By assuming that this variation is entirely due to the ionic charge crossing the cell membrane during the upstroke of an action potential and by considering a typical membrane capacitance of 1 μF/cm$^2$, a value of about 300 μm$^2$ for the effective area where this charge variation occurs has been computed. This value is consistent with the typical adhesion area of the cardiomyocyte soma, thus indicating the validity of the transduction principle.

Figure 19:
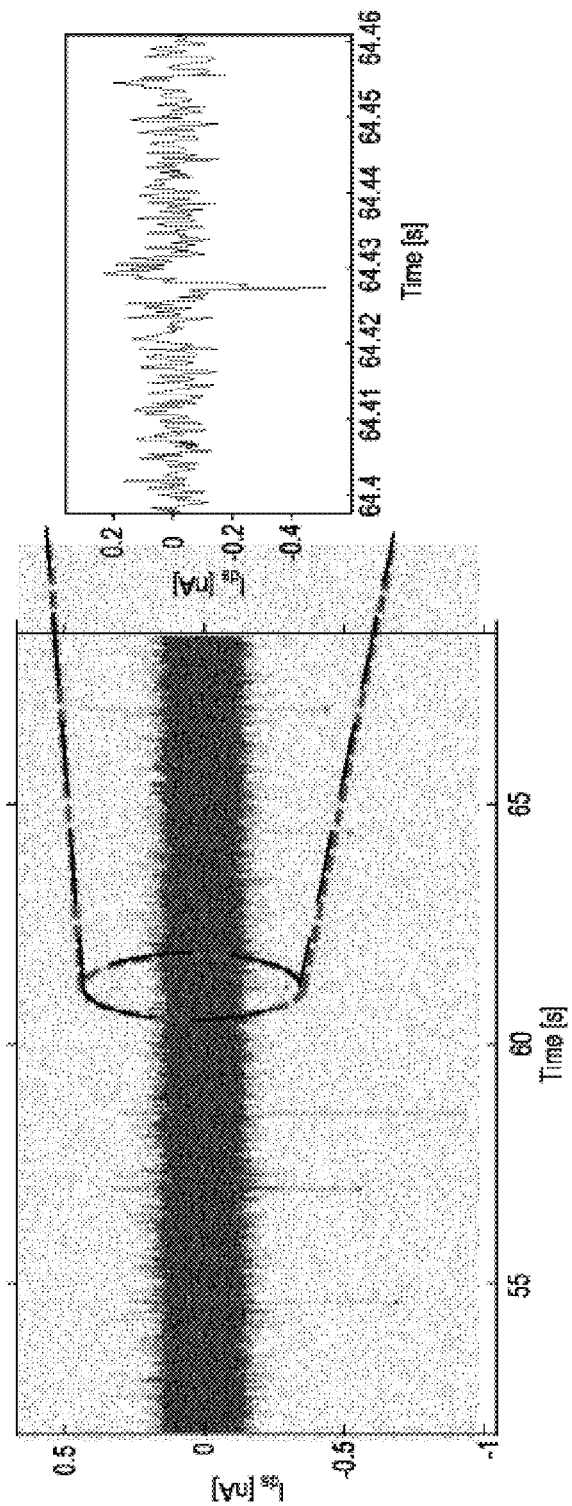
FIG. 19 shows the action potentials of striatal cells from rat embryo (21 DIV) maintained at 37° C. measured with a transistor, and the inset shows a, particular of a neuronal extracellular action potential.

To test the suitability of the system for future applications with neuronal cells, the device was also tested with rat striatal cells. FIG. 19 shows a preliminary recording of the electrical activity of a culture of rat striatal neurons maintained in vitro for 21 days (21 DIV).

In summary, the reliable detection of action potentials (both in physiological conditions and upon stimulation obtained by heating/cooling steps and by pharmacological manipulations) from cardiac cells demonstrates the capability of the reference-less OTFT-based system 100 to efficiently transduce electrophysiological signals from electrogenic cells. The suitability of the proposed system for future applications with neurons was also preliminary successfully tested with rat striatal neurons.

Moreover, a simple working mechanism based on the capacitive coupling between the floating gate of the transistor and the cellular membrane crossed by the ionic charge during the action potential, justifies the observed signal shape and amplitude.

If further data relative to the cells are needed, the system 100 of the invention can also detect additional parameters of the cells. One or more of the transistors 10 can become sensors of cells' parameters. For example one of the apertures 24 can be covered with a PVDF layer so that the organic sensor in which the floating gate at the sensing pad 11 is in contact with the PDVF becomes both a temperature and a stress sensor.

Alternatively or in addition, a plasma activated parylene C layer can be deposited on top of another aperture 24 so that the organic sensor in which the floating gate at the sensing pad 11 is in contact with the parylene C layer becomes a pH sensor.

According to a different method of the invention, the system 100 can be used to send a stimulus to the cells in the sensing area 20 and at the same time preferably to record or monitor the response to such a stimulus.

Figure 10:
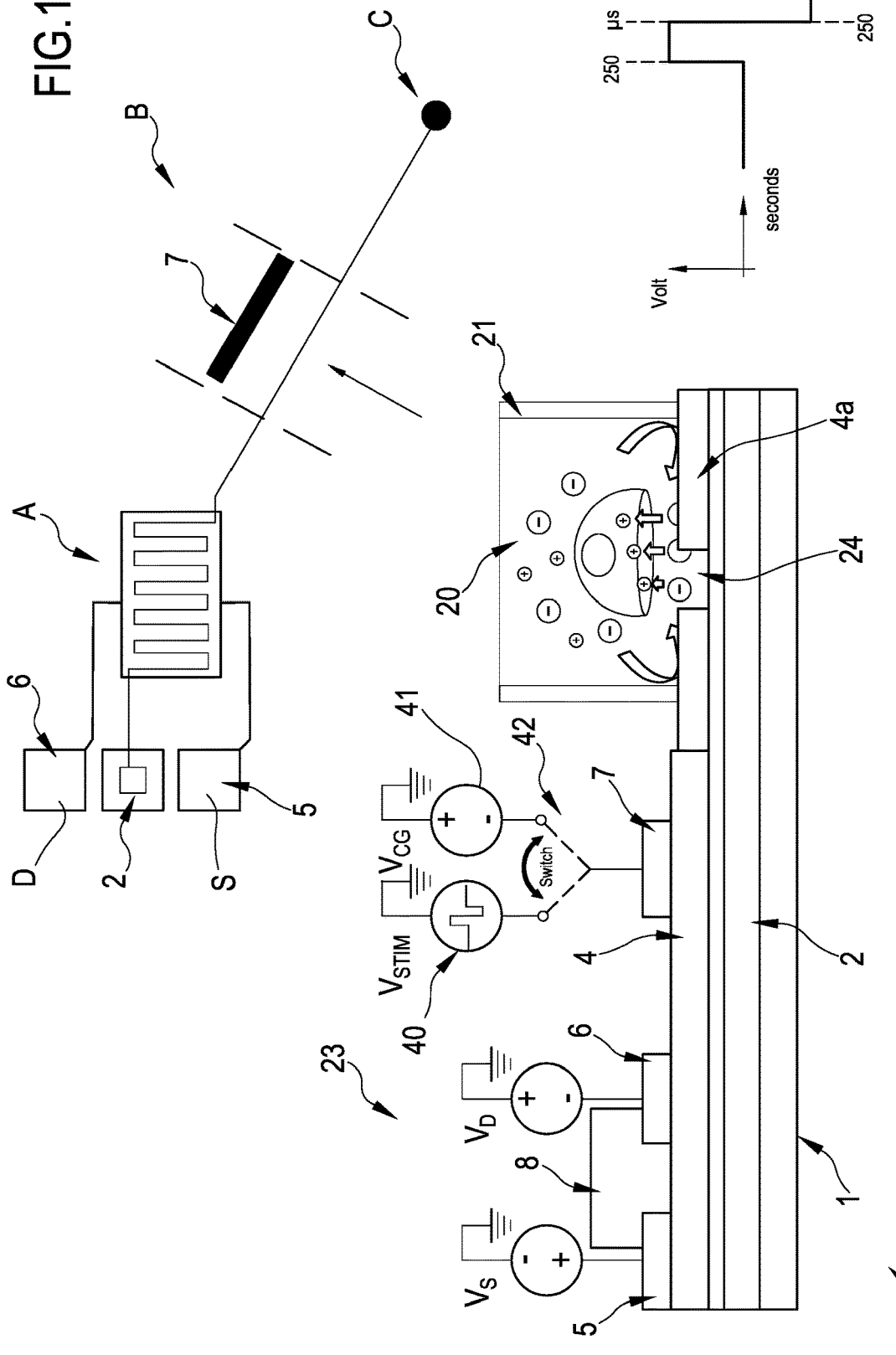
FIGS. 10a and 10b are a top view and a lateral view in section, respectively, of a portion of the system of the invention operating according to a method of the invention.
Figure 11:
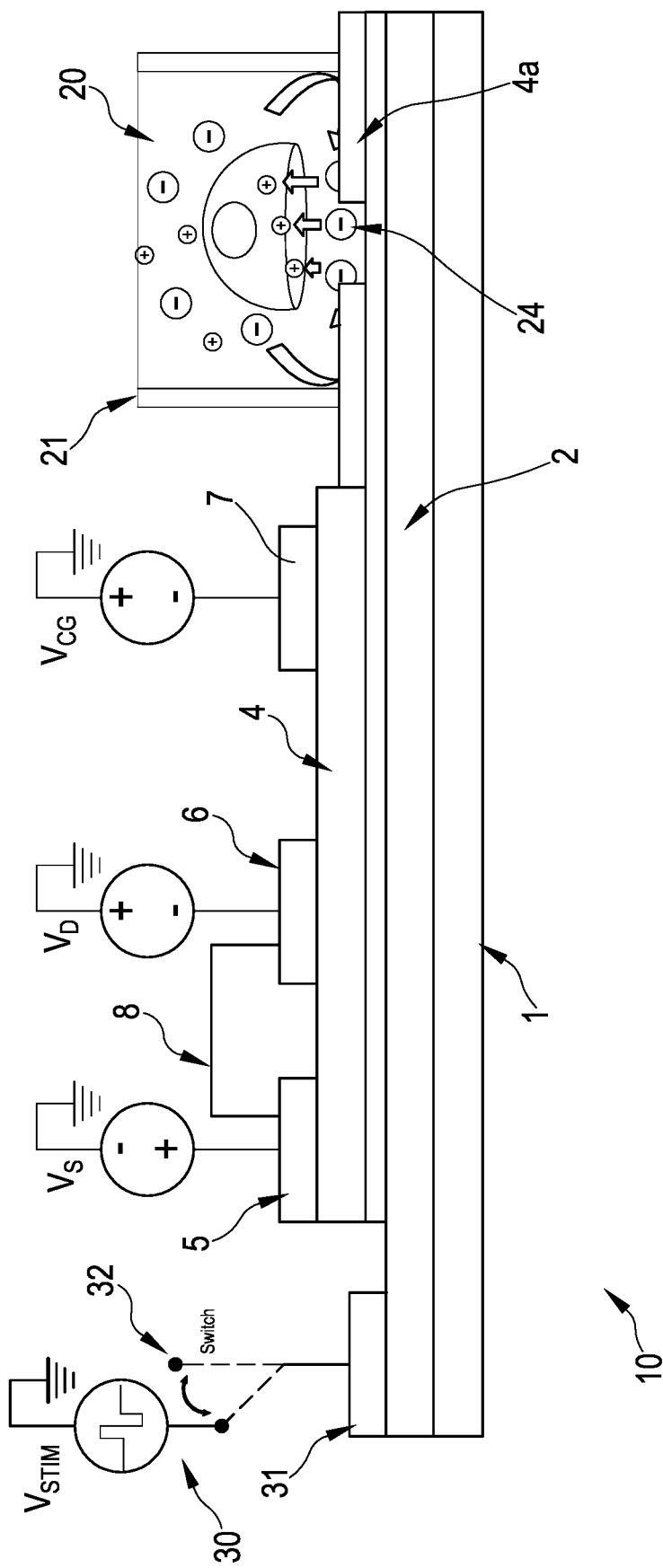
FIG. 11 is a lateral view in section of a variant of the system of the invention for a further embodiment of the method of the invention of FIG. 10b.

With reference to FIGS. 10a, 10b, 11 and 11a, the stimulus to the cells may be imparted by means of the sensing pad 11 (floating gate electrode) of one of the transistors 10, as shown for example in FIG. 11, or by means of the control gate electrode 7 of one of the transistors 10, as shown in FIG. 10b.

In FIG. 10b a back electrode 31 is deposited directly on the floating gate 2. This can be done for example realizing an opening 25 on the insulating layer 4, as shown for example in FIG. 7 and in particular the enlarged FIG. 7a. This opening 25 can be realized in the same manner as apertures 24 are formed.

In both cases, the stimulus is the same, and preferably it is a voltage impulse having the shape depicted in FIG. 11a. The number of impulses depends on the type of experiments and the type of cells. As an example, an impulse each 2-5 seconds is sent and the whole stimulus lasts for 5-10 minutes. The single impulse is a bi-phase impulse, for example lasting in total 500 µs (250 microseconds in the positive range and 250 microseconds in the negative range) and having an amplitude between +/−750 µV and +/−5 V.

In the embodiment of FIG. 11, where the stimulus to the cells is given by means of the floating gate electrode 2 of one of the transistors 10 of the system 100, the impulse of FIG. 11a is generated by an impulse generator 30 which sends the impulse to the floating gate electrode 2 by means of back electrode 31. A switch 32 is present in order to apply or not the impulse to the floating gate depending on the type of measurements, coupling or decoupling the impulse generator 30 to the floating gate electrode 2. The impulse is given to the cells in a specific position, which is the specific position of the sensing pad 11 of the floating gate electrode 2 to which the impulse generator 30 is coupled.

The remaining sensing pads 11 of the other floating gates 2 sense the reaction of the cells present in the sensing area 20 due to the stimulus, monitoring the activity of the cells as above described. Knowing the positions of all sensing pads 11, it is possible to create a two-dimensional map of the response to the stimulus.

In the embodiment of FIG. 10b, where the stimulus is given to the cells in the sensing area 20 by means of a control gate electrode 7 of one of the transistors 10, a stimulus generator 40 and a constant voltage generator 41 (the voltage of the constant generator is however variable in amplitude) are alternatively biasing the control gate electrode 7 depending on the status of a switch 42. The impulse is given to the cells in a specific position, which is the specific position of the sensing pad 11 of the floating gate 2 to which the impulse generator 40 is coupled by means of the capacitor created with the control gate electrode 7.

The remaining sensing pads 11 of the other floating gates 2 sense the reaction of the cells present in the sensing area 20 due to the stimulus, monitoring the activity of the cells as above described.

In this way, a specific location of the sensing area can be stimulated and a mapping of the response, i.e. sensing not only the type of response but the response spatial distribution, can be performed using the system 100.

The invention claimed is:

1. An organic transistor-based system for electrophysiological monitoring of cells including:
a transistor area including a plurality of organic transistors, each organic transistor of the plurality comprising:
a floating gate electrode;
a source electrode and a drain electrode;
an organic semiconductor;
an insulating layer provided between said source and drain electrodes, and said floating gate electrode, said insulating layer having either a thickness comprised between about 1 nm and about 100 nm or a capacitance per unit area comprised between about 10 nF/cm$^2$ and about 150 nF/cm$^2$;
a sensing area, said sensing area including a biocompatible layer including an insulating biocompatible material, said biocompatible layer being apt to be in contact with said cells to be monitored and covering a first portion of floating gate electrodes of the plurality of organic transistors, said biocompatible layer including a plurality of through apertures, each aperture exposing a portion of the floating gate electrode of an organic transistor of the plurality, so that the floating gates of at least some of the organic transistors are exposed in said sensing area in order to be in contact with said cells to be monitored;
a barrier mechanically separating said sensing area and the transistor area;
each of said organic transistors of said plurality further including a control gate electrode coupled to a second portion of said floating gate electrode external to said sensing area by a capacitor, said control gate electrode being separated from said floating gate electrode by said insulating layer, said control gate electrode being apt to set a working point of the organic transistor to which the control gate electrode belongs to by a control voltage ($V_{GS}$) applied to it;
wherein, in each organic transistor, an overlapping area defined by said control gate electrode formed above said floating gate is comprised between 9*10$^{-4}$ cm$^2$ and 2*10$^{-3}$ cm$^2$.

2. The system according to claim 1, including a comparing element apt to select a plurality of said control voltages ($V_{GS}$), each control voltage being applied to a respective control gate electrode of each of the organic transistors of the plurality, said control voltages ($V_{GS}$) being so selected that all organic transistors in the plurality have all a substantially identical drain current ($I_{DS}$) when the cells activity is not monitored.

3. The system according to claim 1, wherein said control voltage is a voltage applied between said control electrode and said source electrode.

4. The system according to claim 1, wherein an area of each said aperture in said biocompatible layer is comprised between 4*10$^{-4}$ mm$^2$ and 8*10$^{-3}$ mm$^2$.

5. The system according to claim 1, wherein one of said apertures in said biocompatible layer is covered by a piezoelectric material layer, said piezoelectric material layer being deposited above a floating gate of an organic transistor of said plurality, so that said organic transistor is apt to be used as a mechanical stress sensor.

6. The system according to claim 1, wherein one of said apertures in said biocompatible layer is covered by a pyroelectric material layer, said pyroelectric material layer being deposited above a floating gate of an organic transistor of said plurality, so that said organic transistor is apt to be used as a temperature sensor.

7. The system according to claim 1, wherein one of said apertures is covered by one of said apertures is covered by a layer of a material which protonize/deprotonize under pH variations, said layer being deposited above a floating gate of an organic transistor of said plurality, so that said organic transistor is apt to be used as a pH sensor.

8. The system according to claim 1, wherein said biocompatible layer includes a poly(p-xylylene) polymer, polyimide, metal oxide or any combination thereof.

9. The system according to claim 1, wherein superposition between source electrode, drain electrode and floating gate electrode is less than 3% of a channel area (W×L) wherein L is defined as a distance between the source and the drain electrodes and W is the width of the source and/or the drain electrode.

10. The system according to claim 1, wherein said plurality of organic transistors includes at least eight organic transistors.

11. The system according to claim 1, including a substrate on which said floating gate electrode is formed, said substrate including a flexible plastic material.

12. The system according to claim 11, wherein said substrate is at least partially transparent to visible radiation.

13. The system according to claim 1, wherein said floating gate electrode includes Ti, $TiO_2$, TiN, indium tin oxide (ITO) or other transparent conductive oxides, conductive polymer, and any combination thereof.

14. The system according to claim 1, wherein said insulating layer includes halogenated poly(p-xylylene) polymer.

15. The system according to claim 1, wherein said source and/or drain electrode includes gold.

16. The system according to claim 1, wherein said floating gate electrode has an interdigitated configuration.

17. A method to detect activity of cells, said cells being positioned onto a sensing area, by a system according to claim 1, the method comprising the steps of:
setting a working point of each organic transistor applying a voltage ($V_{GS}$) to the respective control gate electrode belonging to each organic transistor;
measuring the drain current ($I_{DS}$) of each organic transistor of the plurality;
checking the variations of the drain current ($I_{DS}$) caused by charge re-distribution in the floating gate electrode due to electrophysiological activity of the cells.

18. The method according to claim 17, wherein said working point for all organic transistors of said plurality is such that drain currents ($I_{DS}$) of said organic transistors of said plurality are substantially identical.

19. The method according to claim 17, wherein for each organic transistor of said plurality it includes the steps of:
applying a potential difference ($V_{DS}$s) between drain and source electrodes comprised between $0<V_{DS}\leq3$ Volt; and/or
applying a potential difference ($V_{GS}$) between said control gate electrode and said source electrode comprised between $0<V_{GS}\leq3$ Volt.

20. The method according to claim 17, comprising:
covering one of the apertures with a pyroelectric material layer;
measuring a temperature of said cells by the organic transistor having the floating gate at least partially covered with said pyroelectric material.

21. The method according to claim 17, comprising:
covering one of the apertures with a piezoelectric material layer;
measuring a mechanical stress of said cells by the organic transistor having the floating gate at least partially covered by said piezoelectric material.

22. The method according to claim 17, comprising:
covering one of the apertures with a layer including a material which protonize/deprotonize under pH variations;
measuring a pH of said cells by the organic transistor having the floating gate covered by said layer.

23. Method to send an electrical stimulus to a plurality of living cells deposited on a system, said system according to claim 1, said method including the steps of sending a stimulus to said cells by said floating gate electrode of one organic transistor of said plurality or by said control gate electrode of one organic transistor of said plurality.

24. The method according to claim 23, further including the step of detecting a response of said cells to said stimulus by the first portions of the floating gate electrodes of the remaining organic transistors of said plurality.

25. The method according to claim 24, wherein detecting a response to said stimulus includes:
two-dimensionally mapping said responses to said stimulus, said mapping including locating the position of each first portion of said floating gate of each organic transistor detecting a response.

26. The method according to claim 23, including:
depositing a back contact onto the floating gate of one organic transistor;
sending a stimulus to the cells via the back contact.

* * * * *